(12) United States Patent
Hung et al.

(10) Patent No.: US 9,353,342 B2
(45) Date of Patent: May 31, 2016

(54) CELL CULTURE AND GRADIENT MIGRATION ASSAY METHODS AND DEVICES

(71) Applicant: EMD Millipore Corporation, Billerica, MA (US)

(72) Inventors: Ju-Sung Paul Hung, Billerica, MA (US); Philip J. Lee, Billerica, MA (US); Amedeo J. Cappione, III, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/761,130

(22) Filed: Feb. 6, 2013

(65) Prior Publication Data

US 2013/0171682 A1 Jul. 4, 2013

Related U.S. Application Data

(63) Continuation-in-part of application No. 13/011,857, filed on Jan. 21, 2011, which is a continuation-in-part of application No. 13/436,992, filed on Apr. 1, 2012.

(60) Provisional application No. 61/761,227, filed on Feb. 5, 2013, provisional application No. 61/297,278, filed on Jan. 21, 2010, provisional application No. 61/471,103, filed on Apr. 1, 2011.

(51) Int. Cl.
*C12Q 1/02* (2006.01)
*C12M 1/00* (2006.01)
*C12M 3/06* (2006.01)
*C12M 1/34* (2006.01)

(52) U.S. Cl.
CPC ............. *C12M 27/18* (2013.01); *C12M 23/16* (2013.01); *C12M 41/46* (2013.01); *C12Q 1/02* (2013.01); *C12Q 1/025* (2013.01)

(58) Field of Classification Search
None
See application file for complete search history.

(56) References Cited

U.S. PATENT DOCUMENTS

| | | | |
|---|---|---|---|
| 4,055,613 A | 10/1977 | Kapral | |
| 4,661,455 A | 4/1987 | Hubbard | |
| 4,734,373 A | 3/1988 | Bartal | |
| 4,748,124 A | 5/1988 | Vogler | |
| 5,079,168 A | 1/1992 | Amiot | |
| 5,153,131 A | 10/1992 | Wolf et al. | |
| 5,310,676 A | 5/1994 | Johansson et al. | |
| 5,330,908 A | 7/1994 | Spaulding | |
| 5,376,252 A | 12/1994 | Ekstrom et al. | |
| 5,416,022 A | 5/1995 | Amiot | |
| 5,424,209 A | 6/1995 | Kearney | |
| 5,437,998 A | 8/1995 | Schwarz et al. | |
| 5,451,524 A | 9/1995 | Coble et al. | |
| 5,462,874 A | 10/1995 | Wolf et al. | |
| 5,565,353 A | 10/1996 | Klebe et al. | |
| 5,589,112 A | 12/1996 | Spaulding | |
| 5,593,814 A | 1/1997 | Matsuda et al. | |
| 5,602,028 A | 2/1997 | Minchinton | |
| 5,627,070 A | 5/1997 | Gruenberg | |
| 5,637,469 A | 6/1997 | Wilding et al. | |
| 5,641,644 A | 6/1997 | Klebe | |
| 5,658,797 A | 8/1997 | Bader | |
| 5,686,301 A | 11/1997 | Falkenberg et al. | |
| 5,686,304 A | 11/1997 | Codner | |
| 5,693,537 A | 12/1997 | Wilson et al. | |
| 5,702,941 A | 12/1997 | Schwarz | |
| 5,714,384 A | 2/1998 | Wilson et al. | |
| 5,763,261 A | 6/1998 | Gruenberg | |
| 5,763,275 A | 6/1998 | Nagels et al. | |
| 5,763,279 A | 6/1998 | Schwarz et al. | |
| 5,786,215 A | 7/1998 | Brown et al. | |
| 5,793,440 A | 8/1998 | Nakasaka et al. | |
| 5,801,054 A | 9/1998 | Kiel et al. | |
| 5,866,345 A | 2/1999 | Wilding et al. | |
| 5,882,918 A | 3/1999 | Goffe | |
| 5,900,361 A | 5/1999 | Klebe | |
| 5,912,177 A | 6/1999 | Turner et al. | |
| 5,924,583 A | 7/1999 | Stevens et al. | |
| 5,932,315 A | 8/1999 | Lum et al. | |
| 5,942,443 A | 8/1999 | Parce et al. | |
| 6,039,897 A | 3/2000 | Lochhead et al. | |
| 6,048,498 A | 4/2000 | Kennedy | |
| 6,096,532 A | 8/2000 | Armstrong et al. | |
| 6,107,085 A | 8/2000 | Coughlin et al. | |
| 6,153,073 A | 11/2000 | Dubrow et al. | |
| 6,190,913 B1 | 2/2001 | Singh | |

(Continued)

FOREIGN PATENT DOCUMENTS

| | | |
|---|---|---|
| DE | 19948087 A1 | 5/2001 |
| EP | 0155237 A2 | 9/1985 |

(Continued)

OTHER PUBLICATIONS

Cheng, S.-Y., Heilman, S., Wasserman, M., Archer, S., Shulerac, M.L., and Wu, M. "A hydrogel-based microfluidic device for the studies of directed cell migration", Lab on a Chip 2007, vol. 7, pp. 763-769.*
Park, J.Y., Hwang, C.M., Lee, S.H., and Lee, S-H. "Gradient generation by an osmotic pump and the behavior of human mesenchymal stem cells under the fetal bovine serum concentration gradient", Lab on a Chip 2007, vol. 7, pp. 1673-1680.*
Liu, Y., Sai, J., Richmond, A., and Wikswo, J.P. "Microfluidic switching system for analyzing chemotaxis responses of wortmannin-inhibited HL-60 cells", Biomed Microdevices 2008, vol. 10, p. 499-507.*
Kim, D., Lokuta, M.A., Huttenlocher, A., and Beebe, D.J. "Selective and tunable gradient device for cell culture and chemotaxis study", Lab on a Chip 2009, vol. 9, p. 1797-1800.*
Brinkhof, B., Roelen, B.A.J., and Haagsman, H.P. "Meet the Stem Cells", In Engineering Aspects of Food Biotechnology, Chapter 5; CRC Press: Boca Raton, FL, 2004; p. 127.*

(Continued)

*Primary Examiner* — Renee Claytor
*Assistant Examiner* — Michelle F Paguio Frising
(74) *Attorney, Agent, or Firm* — Nields, Lemack & Frame, LLC

(57) ABSTRACT

A number of novel improved microfluidic configurations and systems and methods of manufacture and operation for a microfluidic invasion assay system.

26 Claims, 28 Drawing Sheets

(56) References Cited

U.S. PATENT DOCUMENTS

| | | |
|---|---|---|
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,251,343 B1 | 6/2001 | Dubrow et al. |
| 6,274,337 B1 | 8/2001 | Parce et al. |
| 6,277,642 B1 | 8/2001 | Mentzen et al. |
| 6,297,046 B1 | 10/2001 | Smith et al. |
| 6,323,022 B1 | 11/2001 | Chang et al. |
| 6,326,211 B1 | 12/2001 | Anderson et al. |
| 6,403,369 B1 | 6/2002 | Wood |
| 6,410,309 B1 | 6/2002 | Barbera-Guillem et al. |
| 6,455,310 B1 | 9/2002 | Barbera-Guillem |
| 6,465,243 B2 | 10/2002 | Okada et al. |
| 6,468,792 B1 | 10/2002 | Bader |
| 6,481,648 B1 | 11/2002 | Zimmermann |
| 6,495,104 B1 | 12/2002 | Unno et al. |
| 6,518,035 B1 | 2/2003 | Ashby et al. |
| 6,534,013 B1 | 3/2003 | Kennedy |
| 6,548,263 B1 | 4/2003 | Kapur et al. |
| 6,551,841 B1 | 4/2003 | Wilding et al. |
| 6,555,365 B2 | 4/2003 | Barbera-Guillem et al. |
| 6,562,616 B1 | 5/2003 | Toner et al. |
| 6,569,675 B2 | 5/2003 | Wall et al. |
| 6,576,458 B1 | 6/2003 | Sarem et al. |
| 6,585,744 B1 | 7/2003 | Griffith |
| 6,585,939 B1 | 7/2003 | Dapprich |
| 6,593,136 B1 | 7/2003 | Geiss |
| 6,637,463 B1 | 10/2003 | Lei et al. |
| 6,648,015 B1 | 11/2003 | Chow |
| 6,653,124 B1 | 11/2003 | Freeman |
| 6,673,595 B2 | 1/2004 | Barbera-Guillem |
| 6,756,019 B1 | 6/2004 | Dubrow et al. |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,821,772 B2 | 11/2004 | Barbera-Guillem |
| 6,846,668 B1 | 1/2005 | Garman et al. |
| 6,857,449 B1 | 2/2005 | Chow |
| 6,908,767 B2 | 6/2005 | Bader |
| 6,915,679 B2 | 7/2005 | Chien et al. |
| 6,969,166 B2 | 11/2005 | Clark et al. |
| 7,005,292 B2 | 2/2006 | Wilding et al. |
| 7,018,830 B2 | 3/2006 | Wilding et al. |
| 7,022,518 B1 | 4/2006 | Feye |
| 7,067,263 B2 | 6/2006 | Parce et al. |
| 7,141,386 B2 | 11/2006 | Dunfield et al. |
| 7,155,344 B1 | 12/2006 | Parce et al. |
| 7,160,687 B1 | 1/2007 | Kapur et al. |
| 7,171,983 B2 | 2/2007 | Chien et al. |
| 7,192,769 B2 | 3/2007 | Pykett et al. |
| 7,223,371 B2 | 5/2007 | Hayenga et al. |
| 7,343,248 B2 | 3/2008 | Parce et al. |
| 7,745,209 B2 | 6/2010 | Martin et al. |
| 7,919,319 B2 | 4/2011 | Jervis et al. |
| 8,257,964 B2 | 9/2012 | Hung et al. |
| 8,673,625 B2 | 3/2014 | Hung et al. |
| 8,709,790 B2 | 4/2014 | Hung et al. |
| 9,206,384 B2 | 12/2015 | Lee et al. |
| 2002/0039785 A1 | 4/2002 | Schroeder et al. |
| 2002/0108860 A1 | 8/2002 | Staats |
| 2002/0108868 A1 | 8/2002 | Fairbourn et al. |
| 2002/0110905 A1 | 8/2002 | Barbera-Guillem et al. |
| 2002/0177221 A1 | 11/2002 | Nishiguchi et al. |
| 2003/0008388 A1 | 1/2003 | Barbera-Guillem et al. |
| 2003/0008389 A1 | 1/2003 | Carll |
| 2003/0030184 A1 | 2/2003 | Kim et al. |
| 2003/0040104 A1 | 2/2003 | Barbera-Guillem |
| 2003/0124623 A1 | 7/2003 | Yager et al. |
| 2003/0143727 A1 | 7/2003 | Chang |
| 2003/0156992 A1 | 8/2003 | Anderson et al. |
| 2003/0211012 A1 | 11/2003 | Bergstrom et al. |
| 2004/0029266 A1 | 2/2004 | Barbera-Guillem |
| 2004/0043481 A1 | 3/2004 | Wilson |
| 2004/0072278 A1 | 4/2004 | Chou et al. |
| 2004/0096960 A1 | 5/2004 | Burd Mehta et al. |
| 2004/0132175 A1 | 7/2004 | Vetillard et al. |
| 2004/0202579 A1 | 10/2004 | Larsson et al. |
| 2004/0229349 A1 | 11/2004 | Daridon |
| 2004/0238484 A1 | 12/2004 | Le Pioufle et al. |
| 2005/0009179 A1 | 1/2005 | Gemmiti et al. |
| 2005/0019213 A1 | 1/2005 | Kechagia et al. |
| 2005/0032208 A1 | 2/2005 | Oh et al. |
| 2005/0072946 A1 | 4/2005 | Studer et al. |
| 2005/0101009 A1 | 5/2005 | Wilson et al. |
| 2005/0106717 A1 | 5/2005 | Wilson et al. |
| 2005/0169962 A1 | 8/2005 | Bhatia et al. |
| 2005/0214173 A1 | 9/2005 | Facer et al. |
| 2005/0221373 A1 | 10/2005 | Enzelberger et al. |
| 2005/0260745 A1 | 11/2005 | Domansky et al. |
| 2005/0266582 A1* | 12/2005 | Modlin et al. ................ 436/164 |
| 2006/0003436 A1 | 1/2006 | DiMilla et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0154361 A1 | 7/2006 | Wikswo et al. |
| 2006/0166354 A1 | 7/2006 | Wikswo et al. |
| 2006/0199260 A1 | 9/2006 | Zhang et al. |
| 2007/0026516 A1 | 2/2007 | Martin et al. |
| 2007/0084706 A1 | 4/2007 | Takayama et al. |
| 2007/0090166 A1 | 4/2007 | Takayama et al. |
| 2007/0122314 A1 | 5/2007 | Strand et al. |
| 2007/0128715 A1 | 6/2007 | Vukasinovic et al. |
| 2007/0264705 A1 | 11/2007 | Dodgson |
| 2007/0275455 A1 | 11/2007 | Hung et al. |
| 2008/0038713 A1 | 2/2008 | Gao et al. |
| 2008/0085556 A1 | 4/2008 | Graefing et al. |
| 2008/0176318 A1 | 7/2008 | Wilson et al. |
| 2008/0194012 A1 | 8/2008 | Lee et al. |
| 2008/0227176 A1 | 9/2008 | Wilson |
| 2008/0233607 A1 | 9/2008 | Yu et al. |
| 2009/0023608 A1 | 1/2009 | Hung et al. |
| 2009/0123961 A1 | 5/2009 | Meyvantsson et al. |
| 2009/0148933 A1 | 6/2009 | Battrell et al. |
| 2009/0203126 A1 | 8/2009 | Hung et al. |
| 2010/0151571 A1 | 6/2010 | Vukasinovic et al. |
| 2010/0196908 A1 | 8/2010 | Opalsky et al. |
| 2010/0234674 A1 | 9/2010 | Wheeler et al. |
| 2012/0003732 A1 | 1/2012 | Hung et al. |
| 2012/0164036 A1 | 6/2012 | Stern et al. |
| 2013/0059322 A1 | 3/2013 | Hung et al. |
| 2013/0081757 A1 | 4/2013 | Hung et al. |
| 2013/0090268 A1 | 4/2013 | Hung et al. |
| 2013/0171679 A1 | 7/2013 | Lee et al. |
| 2014/0057311 A1 | 2/2014 | Kamm et al. |
| 2014/0090735 A1 | 4/2014 | Hung et al. |
| 2014/0099705 A1 | 4/2014 | Hung et al. |
| 2014/0287489 A1 | 9/2014 | Lee et al. |

FOREIGN PATENT DOCUMENTS

| | | |
|---|---|---|
| EP | 0725134 A2 | 8/1996 |
| EP | 0890636 A1 | 1/1999 |
| GB | 1539263 | 1/1979 |
| WO | 91/15570 A1 | 10/1991 |
| WO | 00/56870 A1 | 9/2000 |
| WO | 00/60352 A1 | 10/2000 |
| WO | 00/78932 A1 | 12/2000 |
| WO | 01/92462 A1 | 12/2001 |
| WO | 03/085080 A1 | 10/2003 |
| WO | 03/098218 A1 | 11/2003 |
| WO | 2004/059299 A1 | 7/2004 |
| WO | 2004/106484 A2 | 12/2004 |
| WO | 2005/035728 A2 | 4/2005 |
| WO | 2007/008606 A1 | 1/2007 |
| WO | 20071008609 A2 | 1/2007 |
| WO | 2009/089189 A2 | 7/2009 |
| WO | WO 2009102453 A2 * | 8/2009 |

OTHER PUBLICATIONS

Optics Express, vol. 14, No. 13, Jun. 2006, pp. 6253-6256, "Fabrication of polymer microlens arrays using capillary forming with a

(56) References Cited

OTHER PUBLICATIONS soft mold of micro-holes array and UV-curable polymer", Chang, et al.
Lab Chip, 2007, vol. 7, pp. 641-643, published by The Royal Society of Chemistry, "Rapid fabrication of microchannels using microscale plasma activated templating (uPLAT) generated water molds", Chao, et al.
J. Biochem., vol. 130, pp. 367-376, (2001), "A Method for Micrometer Resolution Patterning of Primary Culture Neurons for SPM Analysis", Degenaar, et al.
Lab Chip, 2003, vol. 3, pp. 318-323, published by the The Royal Society of Chemistry, "Fabrication of microfluidic mixers and artificial vasculatures using a high-brightness diode-pumped Nd: YAG laser direct write method", Lim, et al.
Angew. Chem. Int. Ed., 2004, vol. 43, pp. 1531-1536, "Minimal Functional Model of Hemostasis in a Biomimetic Microfluidic System", Runyon, et al.
Biomedical Microdevices, 2003, vol. 5, No. 3, pp. 235-244, "Microfluidic Patterning of Cellular Biopolymer Matrices for Biomimetic 3-D Structures", Tan, et al.
Extended European Search Report mailed Apr. 3, 2012 in European patent application No. EP 06786499.
International Search Report and Written Opinion mailed Apr. 9, 2009 in PCT application No. PCT/US06126364 (corresponding to U.S. Appl. No. 11/994,997).
International Search Report and Written Opinion mailed Jul. 30, 2009 in PCT application No. PCT/US2009/030168.
Extended European Search report mailed Oct. 21, 2013 in European patent application No. EP 09701350.
International Search Report mailed May 14, 2013 in corresponding PCT application No. PCT/US2013/024999.
International Search Report mailed Mar. 19, 2013 in PCT application No. PCT/US2012/067632.
Cellasic Corporation, ONIX Application Note, "Microincubator for long term live cell microscopy", Feb. 3, 2012, pp. 1-4.
Lab Chip, 2005, vol. 5, No. 4, pp. 401-406, published by The Royal Society of Chemistry, "Human neural stem growth and differentiation in a gradient-generating microfluidic device", Chung, et al.
Biotechnology and Bioengineering, vol. 89, No. 1, Jan. 5, 2005, pp. 1-8, "Continuous Perfusion Microfluidic Cell Culture Array for High-Throughput Cell-Based Assays", Hung, et al.
Lab Chip, 2008, vol. 8, No. 1, pp. 34-57, published by The Royal Society of Chemistry, "Biomolecular gradients in cell culture systems", Keenan, et al.
Biotechnology and Bioengineering, vol. 97, No. 5, Aug. 1, 2007, pp. 1340-1346, "An Artificial Liver Sinusoid With a Microfluidic Endothelial-Like Barrier for Primary Hepatocyte Culture", Lee, et al.
Lab Chip, 2009, vol. 9, No. 1, pp. 164-166, published by The Royal Society of Chemistry, "Dynamic cell culture: a microfluidic function generator for live cell microscopy", Lee, et al.
Journal of the Association for Laboratory Automation (JALA), 2007, vol. 12, No. 6, pp. 363-367, "Microfluidic System for Automated Cell-Based Assays", Lee, et al.
Biomaterials, 2008, vol. 29, No. 22, pp. 3237-3244, "A gel-free 3D microfluidic cell culture system", Ong, et al.
Office Action mailed Apr. 25, 2013 in co-pending U.S. Appl. No. 13/602,328.
Notice of Allowance mailed Oct. 28, 2013 in co-pending U.S. Appl. No. 13/602,328.
Office Action mailed Jun. 17, 2010 in co-pending U.S. Appl. No. 12/019,857.
Final Rejection mailed Feb. 28, 2011 in co-pending U.S. Appl. No. 12/019,857.
Office Action mailed Sep. 15, 2011 in co-pending U.S. Appl. No. 12/019,857.
Final Rejection mailed May 31, 2012 in co-pending U.S. Appl. No. 12/019,857.
Office Action—Restriction—mailed Jul. 13, 2011 in co-pending U.S. Appl. No. 12/348,907.
Office Action mailed Dec. 23, 2011 in co-pending U.S. Appl. No. 12/348,907.
Final Rejection mailed Sep. 17, 2012 in co-pending U.S. Appl. No. 12/348,907.
Office Action Nov. 28, 2012 in co-pending U.S. Appl. No. 13/011,857.
Final Rejection mailed Aug. 14, 2013 in co-pending U.S. Appl. No. 13/011,857.
Office Action—Restriction—mailed Feb. 22, 2013 in co-pending U.S. Appl. No. 13/436,992.
Office Action mailed Sep. 6, 2013 in co-pending U.S. Appl. No. 13/436,992.
Office Action—Restriction—mailed Oct. 16, 2013 in co-pending U.S. Appl. No. 13/692,869.
Office Action—Restriction—mailed Mar. 9, 2011 in co-pending U.S. Appl. No. 11/994,997.
Office Action mailed Jul. 18, 2011 in co-pending U.S. Appl. No. 11/994,997.
Final Rejection mailed Feb. 8, 2012 in co-pending U.S. Appl. No. 11/994,997.
Office Action mailed Sep. 11, 2013 in co-pending U.S. Appl. No. 11/994,997.
Office Action mailed Feb. 22, 2013 in co-pending U.S. Appl. No. 13/602,331.
Notice of Allowance mailed Nov. 13, 2013 in co-pending U.S. Appl. No. 13/602,331.
Final Rejection mailed Apr. 11, 2014 in co-pending U.S. Appl. No. 13/436,992.
Office Action mailed Mar. 6, 2014 in co-pending U.S. Appl. No. 13/692,869.
Final Rejection mailed Apr. 4, 2014 in co-pending U.S. Appl. No. 11/994,997.
Notice of Allowance mailed Jan. 13, 2014 in co-pending U.S. Appl. No. 13/602,328.
Notice of Allowance mailed Dec. 23, 2013 in co-pending U.S. Appl. No. 13/602,331.
International Preliminary Report on Patentability mailed Jun. 12, 2014 in co-pending PCT application No. PCT/US2012/067632.
Office Action mailed May 13, 2014 in co-pending U.S. Appl. No. 13/011,857.
Notice of Allowance mailed Jul. 2, 2014 in co-pending U.S. Appl. No. 13/692,869.
Office Action mailed Sep. 15, 2014 in corresponding U.S. Appl. No. 14/081,314.
Advisory Action mailed Jul. 24, 2014 in co-pending U.S. Appl. No. 11/994,997.
Notice of Allowance mailed Dec. 22, 2014 in co-pending U.S. Appl. No. 12/348,907.
Office Action mailed Nov. 6, 2014 in co-pending U.S. Appl. No. 13/436,992.
Lab Chip, 2005, vol. 5, pp. 44-48, "A novel high aspect ration microfluidic design to provide a stable and uniform microenvironment for cell growth in a high throughput mammalian cell culture array", Hung et al.
Office Action mailed Jan. 26, 2015 in co-pending U.S. Appl. No. 11/994,997.
Office Action mailed Oct. 7, 2014 in co-pending U.S. Appl. No. 12/019,857.
Final Rejection mailed Oct. 20, 2014 in co-pending U.S. Appl. No. 13/011,857.
Final Rejection mailed Mar. 23, 2015 in co-pending U.S. Appl. No. 13/436,992.
Notice of Allowance mailed Apr. 27, 2015 in co-pending U.S. Appl. No. 12/019,857.
Office Action mailed May 13, 2015 in co-pending U.S. Appl. No. 14/053,688.
Notice of Allowance mailed May 4, 2015 in corresponding U.S. Appl. No. 14/081,314.
Office Action mailed Jun. 19, 2015 in co-pending U.S. Appl. No. 14/221,615.
Notice of Allowance mailed Jun. 22, 2015 in co-pending U.S. Appl. No. 11/994,997.

(56) References Cited

OTHER PUBLICATIONS

Notice of Allowance mailed Jul. 31, 2015 in co-pending U.S. Appl. No. 13/692,869.
Notice of Allowance mailed Aug. 24, 2015 in co-pending U.S. Appl. No. 14/081,314.
Japanese communication, with English translation, dated Nov. 17, 2015 in corresponding Japanese patent application No. 2015-503203.
Keenan et al., "A new method for studying gradient-induced neutrophil desensitization based on an open microfluidic chamber", Lab Chip, 2010, vol. 10, pp. 116-122.
Lee et al., "Microfluidic Systems for Live Cell Imaging", Methods in Cell Biology, 2011, vol. 102, pp. 77-103.
Notice of Allowance mailed Jan. 13, 2016 in co-pending U.S. Appl. No. 14/053,688.
Notice of Allowance mailed Jan. 20, 2016 in co-pending U.S. Appl. No. 12/348,907.
Notice of Allowance mailed Dec. 10, 2015 in co-pending U.S. Appl. No. 12/019,857.
Notice of Allowance mailed Jan. 6, 2016 in co-pending U.S. Appl. No. 14/221,615.
Office action mailed Nov. 20, 2015 in co-pending U.S. Appl. No. 13/436,9923.
European communication dated Jul. 28, 2015 in co-pending European patent application No. 12852539.1.
Notice of Allowance mailed Sep. 21, 2015 in co-pending U.S. Appl. No. 14/053,688.
Notice of Allowance mailed Oct. 13, 2015 in co-pending U.S. Appl. No. 12/348,907.
Office action mailed Oct. 6, 2015 in co-pending U.S. Appl. No. 13/011,857.
Final rejection mailed Mar. 11, 2016 in co-pending U.S. Appl. No. 13/436,992.
Notice of Allowance mailed Feb. 22, 2016 in co-pending U.S. Appl. No. 14/081,314.
Notice of Allowance mailed Mar. 31, 2016 in co-pending U.S. Appl. No. 12/019,857.
Notice of Allowance mailed Apr. 7, 2016 in co-pending U.S. Appl. No. 13/011,857.
Notice of Allowance mailed Apr. 11, 2016 in co-pending U.S. Appl. No. 14/221,615.

* cited by examiner

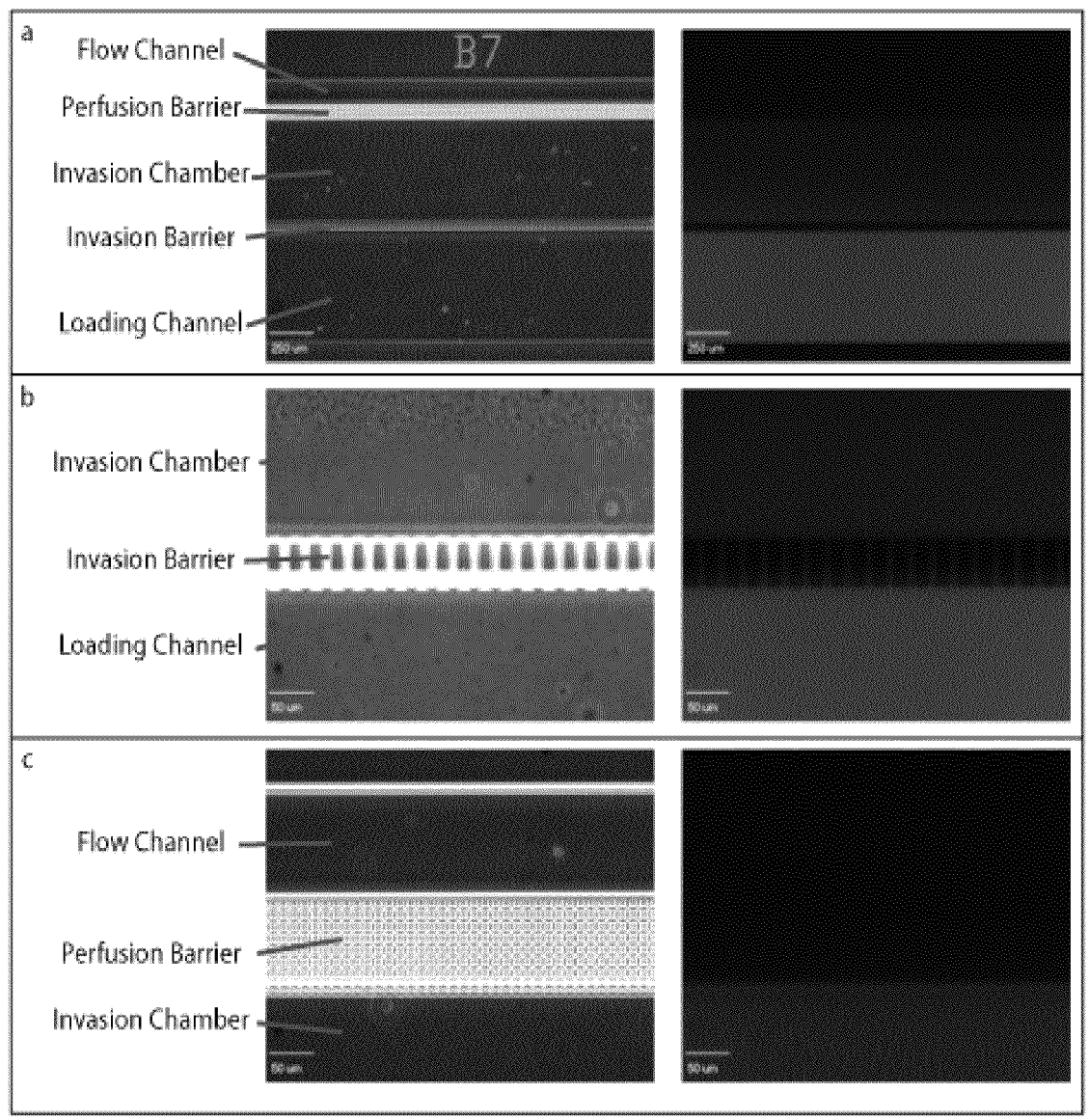
*FIG. 3A-C*

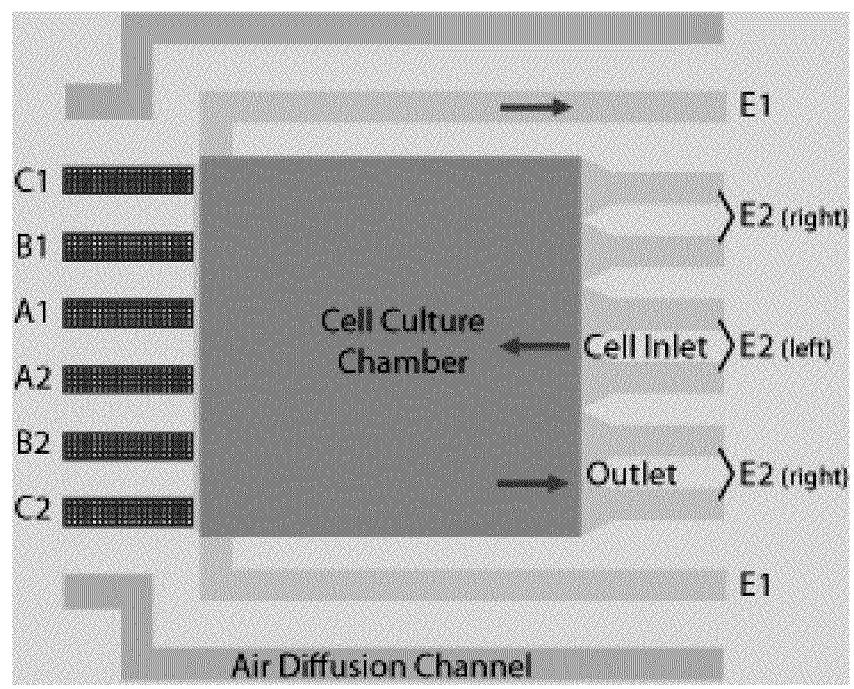
*FIG.6A (SIX WELLS UPSTREAM)*
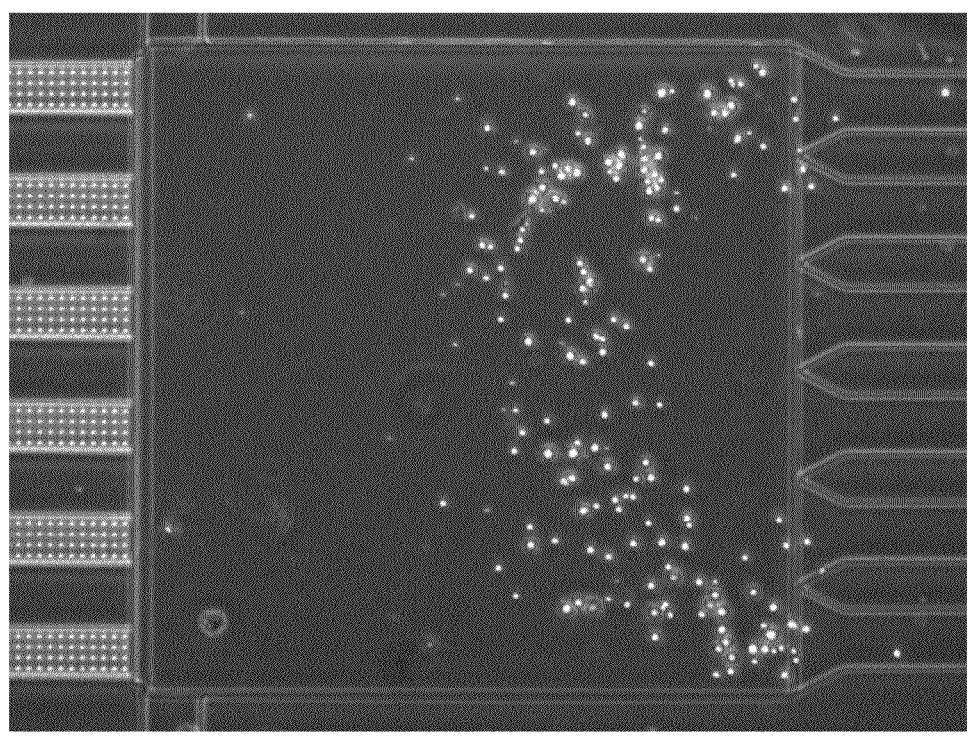
*FIG.6B*

(a)

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 22. (TABLE 1)*

CELL CULTURE AND GRADIENT MIGRATION ASSAY METHODS AND DEVICES

CROSS REFERENCE TO RELATED APPLICATIONS

This application is a continuation-in-part of U.S. patent application Ser. No. 13/011,857, entitled MICROFLUIDIC CELL CULTURE SYSTEMS and filed on Jan. 21, 2011 and which claims priority to 61/297,278, entitled MICROFLUIDIC CELL CULTURE ARRAYS and filed Jan. 21, 2010.

This application is a continuation-in-part of U.S. patent application Ser. No. 13/436,992, entitled Cell CULTURE AND INVASION ASSAY METHOD AND SYSTEM and filed on Apr. 1, 2012 and which claims priority to 61/471,103, entitled CELL CULTURE AND INVASION ASSAY METHOD AND SYSTEMS filed on Apr. 1, 2011. This application also claims priority to 61/761,227, entitled CELL CULTURE AND INVASION ASSAY METHOD AND SYSTEM, filed Feb. 5, 2013.

COPYRIGHT NOTICE

Pursuant to 37 C.F.R. 1.71(e), applicants note that a portion of this disclosure contains material that is subject to copyright protection (such as, but not limited to, diagrams, device photographs, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention in various embodiments relates to assays, systems, and devices for detecting invasion behavior of cells or related behaviors of other micro-objects using microfluidic systems. Particular embodiments involve configurations that can be used with various standard automated handling systems, with active or passive loading and perfusion of medium and to provide high-throughput multi-assay automated systems for analyzing cell invasion, movement, chemotaxis or other properties.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Microfluidic cell culture is an important technology for applications in drug screening, tissue culturing, toxicity screening, and biologic research and can provide improved biological function, higher-quality cell-based data, reduced reagent consumption, and lower cost. High quality molecular and cellular sample preparations are important for various clinical, research, and other applications. In vitro samples that closely represent their in vivo characteristics can potentially benefit a wide range of molecular and cellular applications. Handling, characterization, culturing, and visualization of cells or other biologically or chemically active materials (such as beads coated with various biological molecules) has become increasingly valued in the fields of drug discovery, disease diagnoses and analysis, and a variety of other therapeutic and experimental work.

Numerous aspects related to microfluidic systems, devices, methods and manufacturing are discussed in the above-referenced and related patent applications. While no particular limitations should be read form those applications into any claims presented herein, these incorporated documents provide useful background material related to specific embodiments.

One area of interest in cellular assay systems are assays that are able to determine characteristics of cellular migration. Such assays are important in characterization of various types of malignant cells and also in characterization of other cells under various stimulations.

Some assays using microchambers or microfluidics have been proposed. Other systems use standard culture plates with various barrier inserts to attempt to detect cellular invasion. Currently available systems, however, have failed with regard to a number of aspects necessary for ease-of-use, high-throughput, or automated applications.

Earlier work and patent applications as cited above, discuss various configurations, methods, and systems related to microfluidic cell culture and that work and those publications are incorporated herein by reference.

SUMMARY

The present invention involves various components, systems, and methods related to improved microfluidic cell culture devices and systems, in particular systems for the culturing and analysis of invasive or otherwise metastatic or motile cells. In one aspect, the invention involves novel microfluidic cell culture devices, systems and methods that have advantages over previously proposed invasion or migration or motility assays using either multi-culture chamber plates or microfluidic structures. In another aspect, the invention involves novel structures and methods for integrating multiple microfluidic cell culture and/or cell invasive assay units into various multi cell culture unit systems, such as to a microtiter well plate structure including various standard well plate formats (e.g., a 96-well SBS culture plate, or other plate formats, including plates having 6, 12, 24, 96, 384 or 1536 sample wells, as well as open bottom standard well plates, allowing for attachment to microfluidic structures as described herein.).

In particular embodiments and examples, design features include providing an invasion assay device in a convenient format that allows for the elimination of tubing and connectors to the plates themselves, the ability to maintain long-term continuous perfusion cell culture using a passive gravity-driven flow, the ability to perform direct analysis on the outlet wells and/or cellular invasion observation wells or culture wells of the microfluidic plate, the ability to effectively handle gel culture media.

While many of the examples discussed in detail herein are designed to be used in conjunction with a standard or custom well plate, the microfluidic structures and culture units and systems and methods of various configurations as described herein can also be deployed independently of any well-plate, such as in various integrated lab-on-a-chip systems that are not configured to be used in conjunction with well plates or various other microfluidic devices or systems.

For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. Unless specifically stated otherwise herein, any combination of elements described herein should be understood to include every sub-combination of any subset of those elements and also any sub-combination of any subset of those elements combined with any other element described herein as would be understood to a practitioner of skill in the art.

In some of the drawings and detailed descriptions below, the present invention is described in terms of the important independent embodiments of multi-component devices or systems. This should not be taken to limit various novel aspects of the invention, which, using the teachings provided herein, can be applied to a number of other situations. In some of the drawings and descriptions below, the present invention is described in terms of a number of specific example embodiments including specific parameters related to dimensions of structures, pressures or volumes of liquids, temperatures, electrical values, durations of time, and the like. Except where so provided in the attached claims, these parameters are provided as examples and do not limit the invention, which encompasses other devices or systems with different dimensions. For purposes of providing a more illuminating description, particular known fabrication steps, cell handling steps, reagents, chemical or mechanical process, and other known components that may be included to make a system or manufacture a device according to specific embodiments of the invention are given as examples. It will be understood to those of skill in the art that except were specifically noted herein otherwise, various known substitutions can be made in the processes described herein.

All references, publications, patents, and patent applications cited in this submission are hereby incorporated by reference in their entirety for all purposes.

BRIEF DESCRIPTION OF THE DRAWINGS

FIG. 3A-C are a series of micrographs of regions of the invasion chamber after loading with gel to show invasion assay operation and cellular migration in a gradient according to specific embodiments of the invention.

FIG. 6A-C illustrate configuration and operation of an example roughly rectangular cell culture chamber design and gradient chamber design according to specific embodiments of the invention.

FIG. 22 (Table 1) illustrates an example of diseases, conditions, or states that can evaluated or for which drugs or other therapies can be tested according to specific embodiments of the present invention.

DETAILED DESCRIPTION OF SPECIFIC EMBODIMENTS

1. Overview

Definitions

Figure 1A:
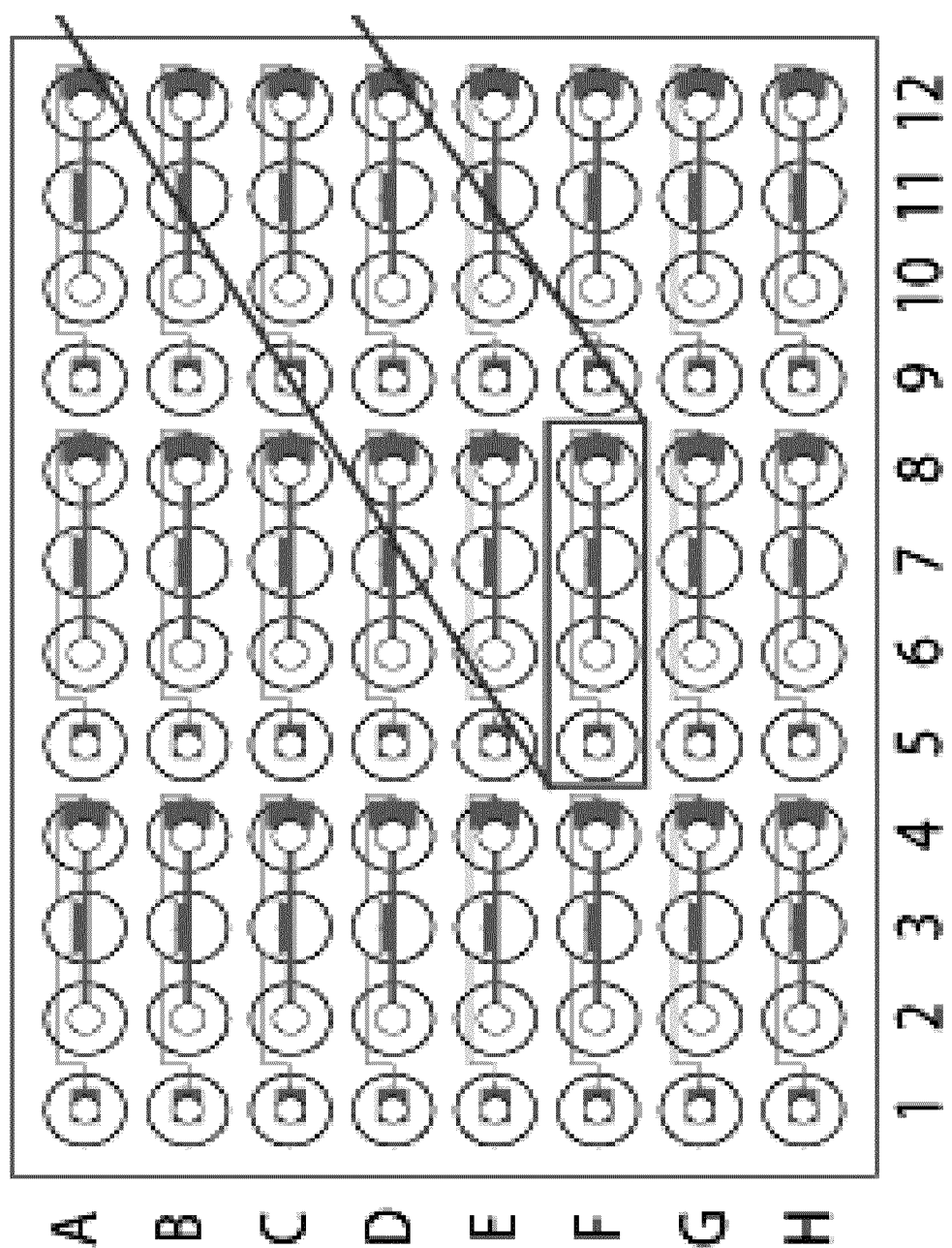
FIG. 1 (A) is a schematic diagram of an example microfluidic plate design according to specific embodiments, in this example having 24 invasion assay units on a 96 well plate, each unit in this example containing 4 wells: a flow inlet, a cell/gel inlet, an invasion chamber, and a flow outlet. (B) is a schematic diagram showing details of one invasion culture unit according to specific embodiments of the invention.

A "particle" refers to biological cells, such as mammalian or bacterial cells, viral particles, or liposomal or other particles that may be subject to assay in accordance with the invention. Such particles have minimum dimensions between about 50-100 nm, and may be as large as 20 microns or more. When used to describe a cell assay in accordance with the invention, the terms "particles" and "cells" may be used interchangeably.

A "microchannel" or "channel" or "flow channel" generally refers to a micron-scale channel used for fluidically connecting various components of systems and devices according to specific embodiments of the invention. A microchannel typically has a rectangular, e.g., square, or rounded cross-section, with side and depth dimensions in a preferred embodiment of between 10 and 500 microns, and 10 and 500 microns, respectively. Fluids flowing in the microchannels may exhibit microfluidic behavior. When used to refer to a microchannel within the microwell array device of the invention, the term "microchannel" and "channel" are used interchangeably. "Flow channel" generally denotes channels designed for passage of media, reagents, or other fluids or gels and in some embodiments cells. "Culture channel" or "cell culture channel" generally denotes a portion of a cell culture structure that cells are designed to flow through and also remain during cell culture (though the cells may be localized into a particular culture area of the culture channel in some embodiments). "Air channel" generally denotes a roughly micron-scale channel used for allowing gases, such as air, oxygen enriched mixtures, etc., to pass in proximity to flow channels or culture areas. "Perfusion channel" is sometimes used to indicate a flow channel and any perfusion passages or structures that allow media to perfuse to the culture area.

A 'barrier' or "diffusion barrier" or "perfusion barrier" or "mass transfer barrier" refers to a combination of solid structures and passages smaller than the flow channels that generally separate a flow channel from a cell culture area or chamber. The passages are generally smaller than the microchannel height and/or width (for example, on the order of 5-50% or on the order of about 10%) and in some embodiments are designed to keep cells, other culture items, and in some embodiments gels, from migrating into the flow channels, while allowing some fluidic flow through diffusion, perfusion, or any combination of mass transfer mechanisms that is generally of a much higher fluidic resistance than the fluid flow in the flow channels. In one example embodiment, the barrier has a passage that is 4 microns high and that otherwise runs most of the length of the microchannel. In other embodiments, a barrier has many passages that are about as high as the microfluidic channel, but about 4 microns wide. A barrier may also allow some migration of cells or cell components through the barrier, or other materials or particles small enough to pass through the passages.

A "microfluidics device" refers to a device having various station or wells connected by micron-scale microchannels in which fluids will exhibit microfluidic behavior in their flow through the channels.

A "microwell array" refers to an array of two or more microwells formed on a substrate.

A "device" is a term widely used in the art and encompasses a broad range of meaning. For example, at its most basic and least elaborated level, "device" may signify simply a substrate with features such as channels, chambers and ports. At increasing levels of elaboration, the "device" may further comprise a substrate enclosing said features, or other layers having microfluidic features that operate in concert or independently. At its most elaborated level, the "device" may comprise a fully functional substrate mated with an object that facilitates interaction between the external world and the microfluidic features of the substrate. Such an object may variously be termed a holder, enclosure, housing, or similar term, as discussed below. As used herein, the term "device" refers to any of these embodiments or levels of elaboration that the context may indicate.

"Any combination" of elements or claims as used herein refers to combinations of the elements references or any individual element referenced.

Microfluidic systems provide a powerful tool to conduct biological experiments. Recently, elastomer-based microfluidics has especially gained popularity because of its optical transparency, gas permeability and simple fabrication methods. However, the interface with the end-users requires labor-intensive hole punching through the elastomer, and additional steps of tubing and syringe pump connection.

The present invention involves integrated microfluidics used for various culture and assay applications. The invention further involves methods of manufacture of microfluidics and components and a system for automating cell culture using such plates. Advantages of specific embodiments include use of a standard microtiter plate format, tubing free cell culture, and a biomimetic microenvironment for assaying invasion, migration, or chemotaxic cellular behavior.

A system according to specific embodiments of the invention (for example, using 96-well standard plates) can be operated using standard techniques and equipment for handling standard microtiter plates, as are well known in the art. For example, liquid and/or gel or cell dispensing is achieved with standard pipette mechanics, and cell culture and analysis can be made compatible with existing incubators and plate readers.

According to further embodiments of the invention, a novel cell loading system uses a pneumatic manifold and pneumatic pressure to place cells in the micro culture area. With the addition of this cell loading system, microfluidic cell culture and analysis can be fully automated using other automated equipment that exists for handling standard titer plates.

In further embodiments, the gravity driven flow culture configuration utilizes the medium level difference between the inlet and outlet well as well as engineering the fluidic resistances to achieve the desirable flow rate in nL/min regime. This provides the significant advantage of being able to "passively" flow culture medium for long periods of time (e.g., up to 4 days) without the use of bulky external pumps or tubes, which in the case of invasive assays allows for easy set up of the assay and easy reading of invasive assay results at one or more time periods after culture initiation.

In further embodiments, the invention involves a microfluidic system to allow control of the cell culture environment for long-term time-lapse microscopy of adherent and/or invasive or migrating cells. According to specific embodiments of the invention, the invention provides a multiplexed microfluidic flow chamber allowing for time-lapse microscopy experimentation and examination of cell invasion among other assays. The microfluidic chamber uses a perfusion barrier to separate cells from flow channels and an invasion barrier to study the invasive properties of cells between an culture chamber and an invasion chamber. Example embodiments are formatted to a standard well plate, allowing liquid and cell/gel samples to be directly pipetted into the appropriate inlet reservoirs using standard equipment.

In some embodiments, a custom pneumatic flow controller can be used to load the cells into the culture regions as well as to switch between different exposure solutions. A digital software interface can be used to allow a user to program specific inputs (pulses, ramps, etc.) over time to expose the cells to complex functions during time-lapse imaging.

Dynamic responses in living cells are the foundation for phenomena such as biological signal processing, gene expression regulation, differentiation, and cell division. In specific embodiments, the invention involves a system capable of controlling the cellular micro-environment in a multiplexed format compatible with current cell culture methods. Cell response can be quantified using high magnification fluorescence microscopy to derive kinetic information with sub-cellular resolution. This capability has broad applications in cellular systems biology where dynamic single cell response experiments are not currently practical. While some invasion assay embodiments according to specific embodiments can use mostly or fully passive systems with exposure to just one medium/reagent mixture other invasion assays according to specific embodiments can be performed using complex reagent scheduling using a manifold as described herein.

2. Microfluidic Culture System and Array

The applications referenced above discussed a variety of different cell culture configurations and fabrication techniques. Portions of the operation of the cell culture areas and materials are useful as background to the present discussion. In some examples therein, one or more micro culture areas are connected to a medium or reagent channel via a grid of fluidic passages (or diffusion inlets or conduits), wherein the grid comprises a plurality of intersecting high fluidic resistance perfusion passages. In one discussed example, passages in the grid are about 1 to 4 µm in height, 25 to 50 µm in length and 5 to 10 µm in width, the grid allowing for more even diffusion between medium or reagent channels and the culture area and allowing for easier manufacturing and more even diffusion. The earlier application further discussed that the high fluidic resistance ratio between the microchamber and the perfusion/diffusion passages or grid (e.g., ratios in the range of about 10:1, 20:1 to 30:1) offers many advantages for cell culture such as: (1) size exclusion of cells; (2) localization of cells inside a microchamber; (3) promoting a uniform fluidic environment for cell growth; (4) ability to configure arrays of microchambers or culture areas; (4) ease of fabrication, and (5) manipulation of reagents without an extensive valve network. Examples were illustrated wherein a grid-like perfusion barrier can be much shorter than the culture area or can be near to or at the same height, according to specific embodiments of the invention and further wherein various configurations for culture devices were illustrated.

3. Invasion Assay Unit

In specific embodiments, the invention further comprises a microfluidic plate for 3D cancer cell invasion assays. In specific example implementations, the plate uses the standard 96 well plate format with 4 wells connected by microfluidic channels to create each individual flow and invasion assay unit (with, e.g., 24 units per plate in specific embodiments). In some embodiments, flows are driven by capillary force and gravity as discussed elsewhere herein, allowing the plates to be operated in a standard incubator with no external connections after initial introduction of cells and culture media. In specific embodiments, a device of the invention receives cells in a 3D gel into a culture chamber. The culture chamber is separated by an invasion barrier from an invasion chamber and both are separated from the flow channel by a set of, for example, 8×8 micron cross section microfluidic pores or passages (at times herein referred to as the invasion barrier) thus modeling the in vivo environment for tumor invasion.

FIG. 1 (A) is a schematic diagram of an example microfluidic plate design according to specific embodiments, in this example having 24 invasion assay units on a 96 well plate, each unit in this example containing 4 wells: a flow inlet, a cell/gel inlet, an invasion chamber, and a flow outlet. In this embodiment, liquid in the flow inlet, cell/gel inlet, and flow outlet are in contact with the microchannels. The well above the invasion chamber is left empty for better imaging quality. The bottom surface of the plate is a glass slide. There are 24 flow units per plate (each unit is 1 well by 4 wells, forming an 8×3 array on the 8×12 well plate).

Figure 1B:
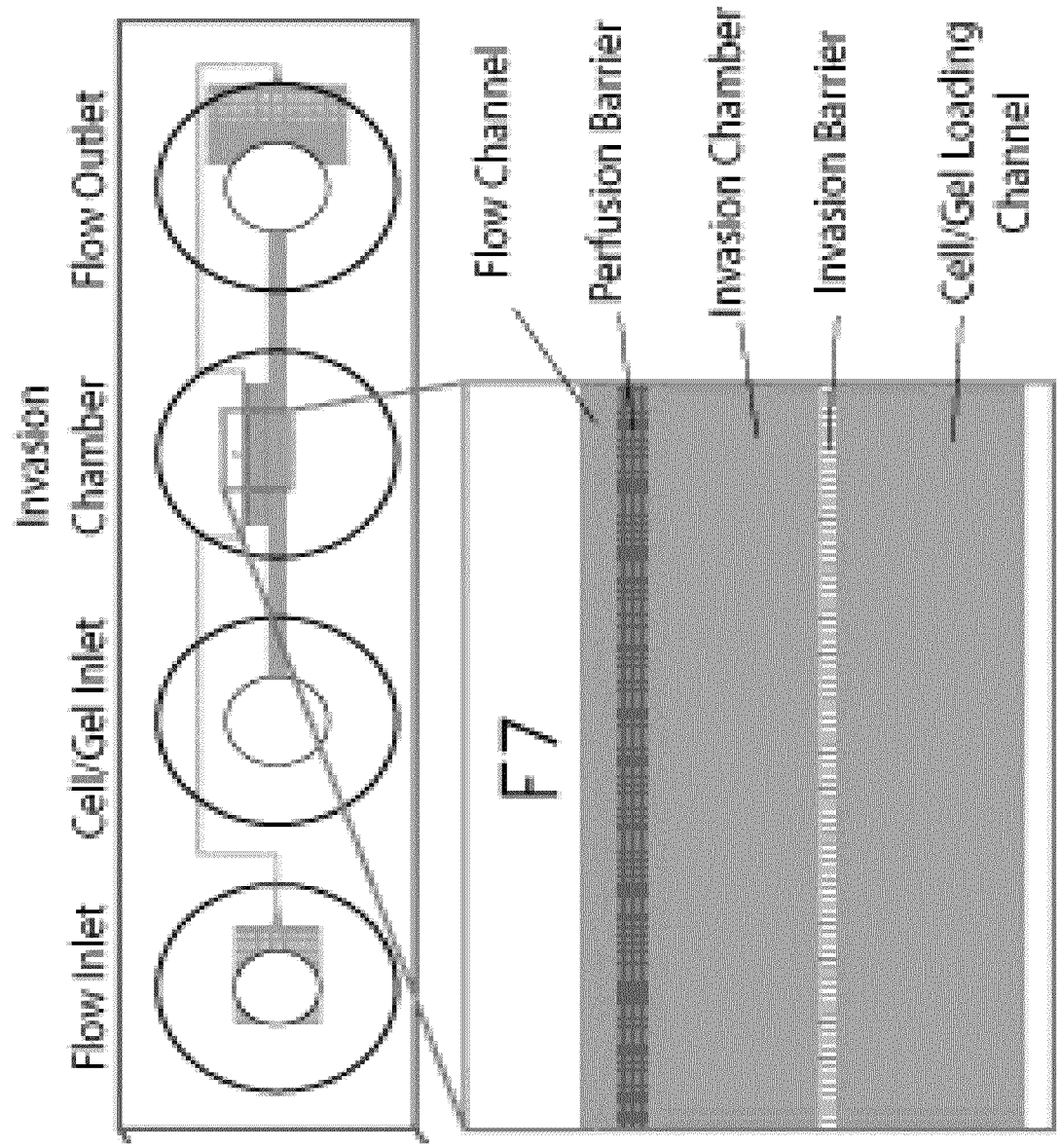

Returning to the schematic shown in FIG. 1A-B, the figure provides three levels of magnification. The most magnified region, labeled F7 in FIG. 1A-B to indicate the particular well position in the example 96 well plate, shows details of one invasion chamber according to specific embodiments. This invasion assay/culture area can be understood as comprising 5 primary regions.

A cell/gel loading channel is shown at the bottom of the figure. According to specific embodiments, cells mixed in a gel (e.g. Matrigel, collagen, fibrin, etc.) are loaded into the bottom channel, either by capillary flow or using other active or passive loading means as described herein. In operation, the channel is designed so that the gel fills the loading channel and also fills the invasion barrier and part or all of the invasion chamber, but not past the perfusion barrier. In one example embodiment, the loading channel is 550 µm in width and 50 µm in height.

According to specific embodiments, the loading channel is separated from an invasion chamber by an invasion barrier. In a specific example, the invasion barrier consists of a network of channels of approximately 50×8×8 µm (L×W×H) dimensions. These are or become filled with gel or liquid in some embodiments and mimic the endothelial barrier in tissue. Invasive cancer cells are able to move through the narrow channels of the invasion barrier into the invasion chamber. The invasion chamber in this example about 4.8×0.5×0.05 mm in dimension (L×W×H) and is used to count the number of cells that invade or migrate from the loading channel past the invasion barrier. During assay operation, cells in this chamber can be counted by manual or automated microscope or other means and quantified to determine an invasion index for the well.

The perfusion barrier is a network of channels of, in specific embodiments, dimensions of 100×4×2 µm (L×W×H), that separates the invasion chamber from the flow channel. The narrow cross section prevents cells and gels from passing through the infusion barrier. Medium (and drugs carried in the medium, including chemoattractants, dyes, or other materials used in an invasion assay or in cell culture) diffuse across the perfusion barrier and form a gradient to the invading cells, modeling the tumor environment in the vasculature.

An 100×50 μm (W×H) flow channel carries fluid from the flow inlet well past the invasion chamber and empties to the flow outlet well. Diffusion of nutrients from the flow through the perfusion barrier feeds the cells. This channel simulates the blood flow in the body. In a particular example embodiment, the gravity driven flow rate is set to ~20 μl/day, allowing for >3 day continuous flow experiments without refilling the wells.

As stated above, dimensions provided herein are for an example culture unit. According to various specific embodiments, any dimensions suitable for a particular media or culture item can be used in accordance with other teachings provided herein.

4. Invasion Assay Plate

According to specific embodiments, the invasion assay unit as described above is configured into a standard culture well plate to allow for simultaneous running of multiple invasion assay experiments. These experiments can include multiple assays for a single subject, either of the same or different tissue samples, multiple assays from different subjects, and can include assays that expose cells to different media, hormonal or other stimuli, drugs, chemoattractants, etc.

While an example of a 4-well assay unit on a 96 well-plate is shown, different unit sizes and different culture plate sizes can also embody the invention as will be clear from the discussions provided herein and in related incorporated applications.

Figure 2A:
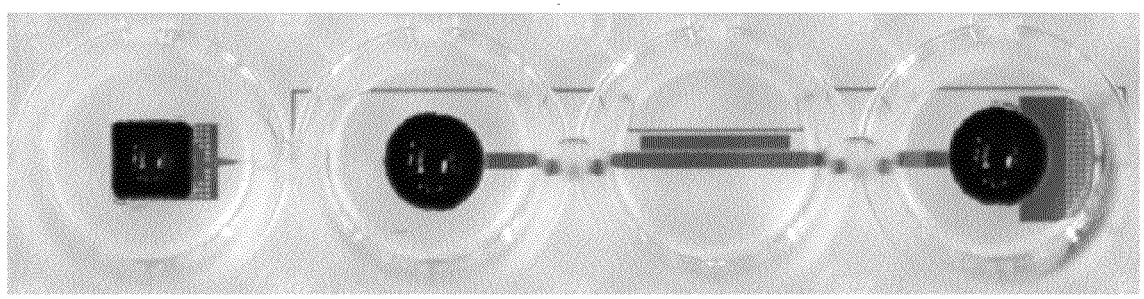
FIG. 2 are photos illustrating an example single flow unit filled with blue dye with the image taken from top (A) and bottom (B), with the bottom picture taken by flipping the plate in the up-down direction, so that the inlet well is on the left in both pictures.
Figure 2B:
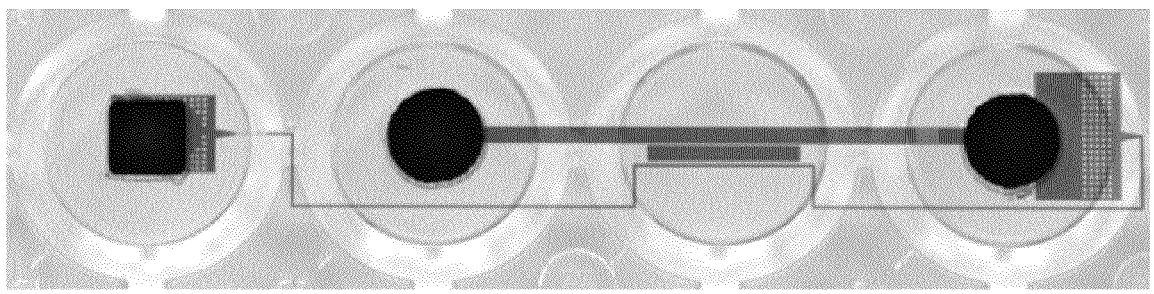

FIG. 2 are photos illustrating an example single flow unit filled with blue dye with the image taken from top (A) and bottom (B), with the bottom picture taken by flipping the plate in the up-down direction, so that the inlet well is on the left in both pictures.

5. Example Operation

FIG. 3A-C are a series of micrographs of regions of the invasion chamber after loading with gel to show invasion assay operation and cellular migration in a gradient according to specific embodiments of the invention. Matrigel mixed with fluorescent dye (red) was loaded by capillary flow into the loading channel and polymerized at 37 C for 15 minutes. FIG. 3A illustrates 40× magnification of the invasion chamber showing the gel fills the loading channel, invasion barriers, and part of the invasion chamber. FIG. 3B shows 200× magnification of the invasion barriers. The polymerized gel can be seen inside the invasion barriers, as well as in the invasion chamber. FIG. 3C shows 200× magnification of the perfusion barrier, showing the gel is unable to cross the narrow channel network. As will be further understood from the teachings herein, the "gel" can have various viscosities down to a fluid viscosity in specific embodiments and specific tests. In specific embodiments, the perfusion barrier allows for use of a wider range of gel viscosities according to the invention.

Figure 4A:
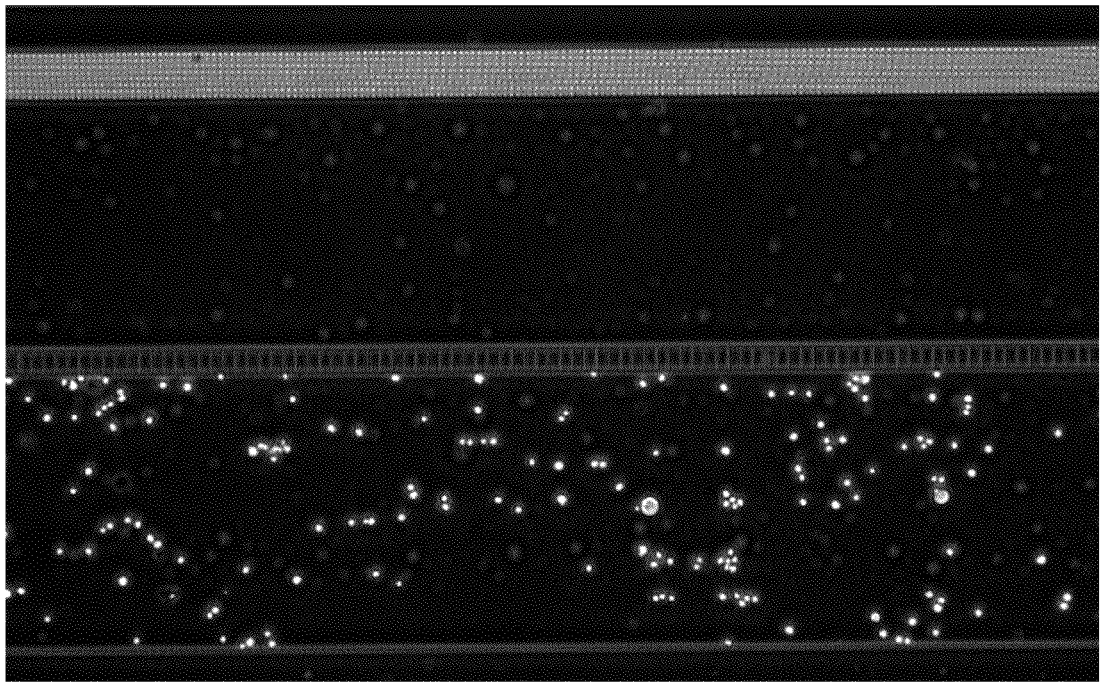
FIG. 4A-B are micrographs showing cancer cell invasion and cellular migration in a gradient in an assay system and device according to specific embodiments of the invention.
Figure 4B:
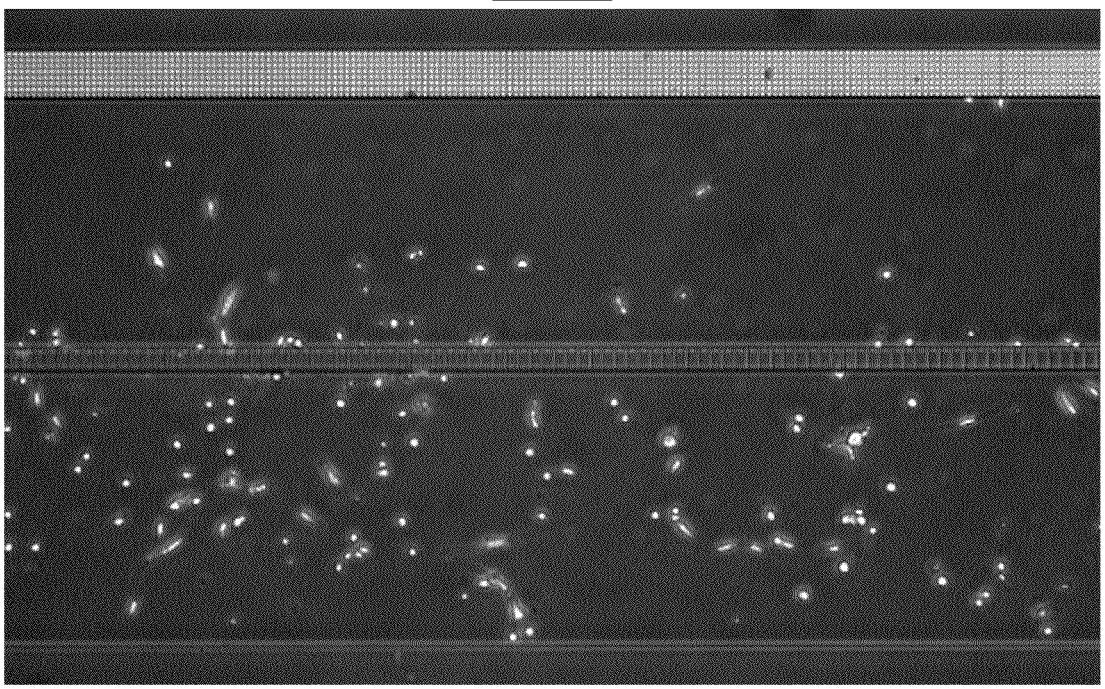

FIG. 4A-B are micrographs showing cancer cell invasion and cellular migration in a gradient in an assay system and device according to specific embodiments of the invention. In this example, HT-1080 invasive human breast cancer cells were loaded in 3D Matrigel and perfused with medium containing 10% serum. FIG. 4A shows cells immediately after loading and polymerization of the gel are located on the bottom side of the invasion barrier. FIG. 4B shows cells after 24 hours of perfusion culture with serum containing medium (known signal for HT-1080 invasion), some of the cells have migrated through the Matrigel and invasion barriers to occupy the invasion chamber. Images taken with phase contrast at 40× magnification.

In further embodiments, various strategies can be used to remove some of all of the cells in the invasion chamber for further analysis. According to specific embodiments, the invention further facilitates this by providing a culture environment in the invasion chamber that sustains the cells until they are removed.

In further embodiments, air diffusion through the material that defines the microfluidic channels (such as silicone elastomer polydime-thylsiloxane (PDMS)) structure into the culture areas can be facilitated by air passages and air holes as described elsewhere herein.

As discussed elsewhere, various modifications may be made to the cell culture area as described above. Various configurations are possible for the perfusion barrier such as a grid-like passage structure. Other variations will be suggested to those of skill in the art having the teachings provided herein.

The structures disclosed above can also be adapted to systems using more or fewer wells on a standard microtiter well plate or a fully customized or partially customized plate, such as those described in referenced documents and in other examples herein.

Plates and systems as described herein can be used with other configurations of cell culture areas and invasion chambers and micro-fluidic flow structures as described in above referenced patent applications. In one modified design, the cell culture area provided is an essentially rectangular cell culture chamber. The cell culture chamber has cell inlet and outlet passages at the right, and flow outlets also at the right. In this example, the cell passages are paired, with the center pair used for cell flow loading and the pairs on either side used as a cell flow outlet.

Once the cells are loaded, the invasion assay proceeds as outlined above, after any invasive cells have had sufficient time to move through the invasion barrier.

Figure 5A:
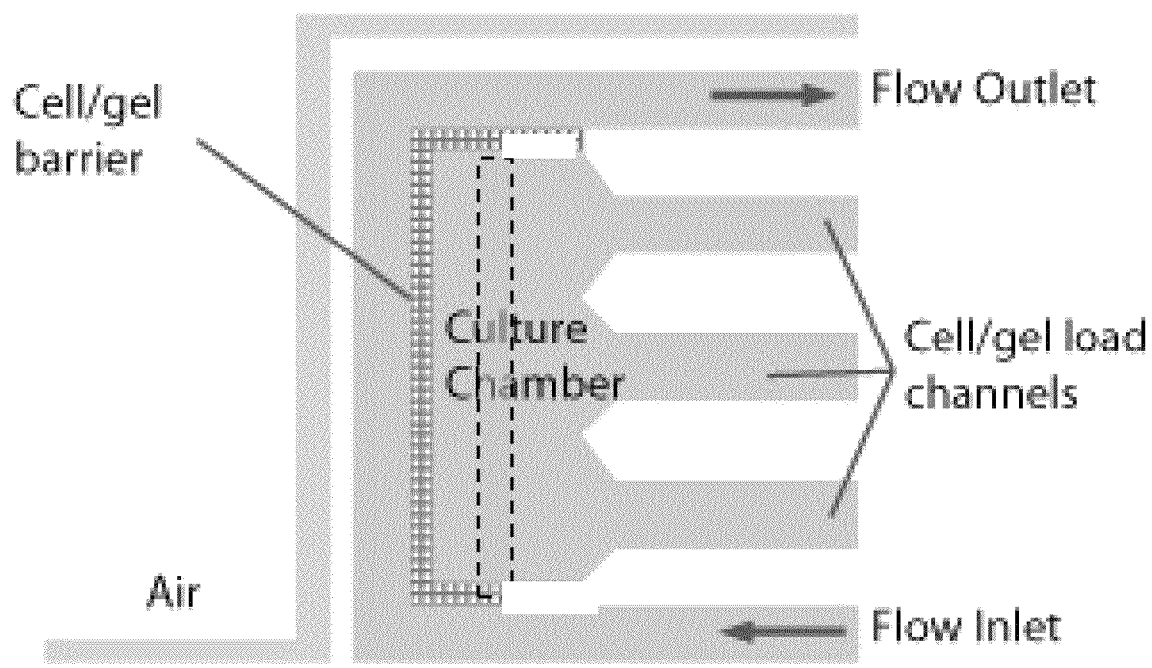
FIG. 5A-B illustrate configuration and operation of an example cell culture chamber design with multiple inlets according to specific embodiments of the invention.
Figure 5B:
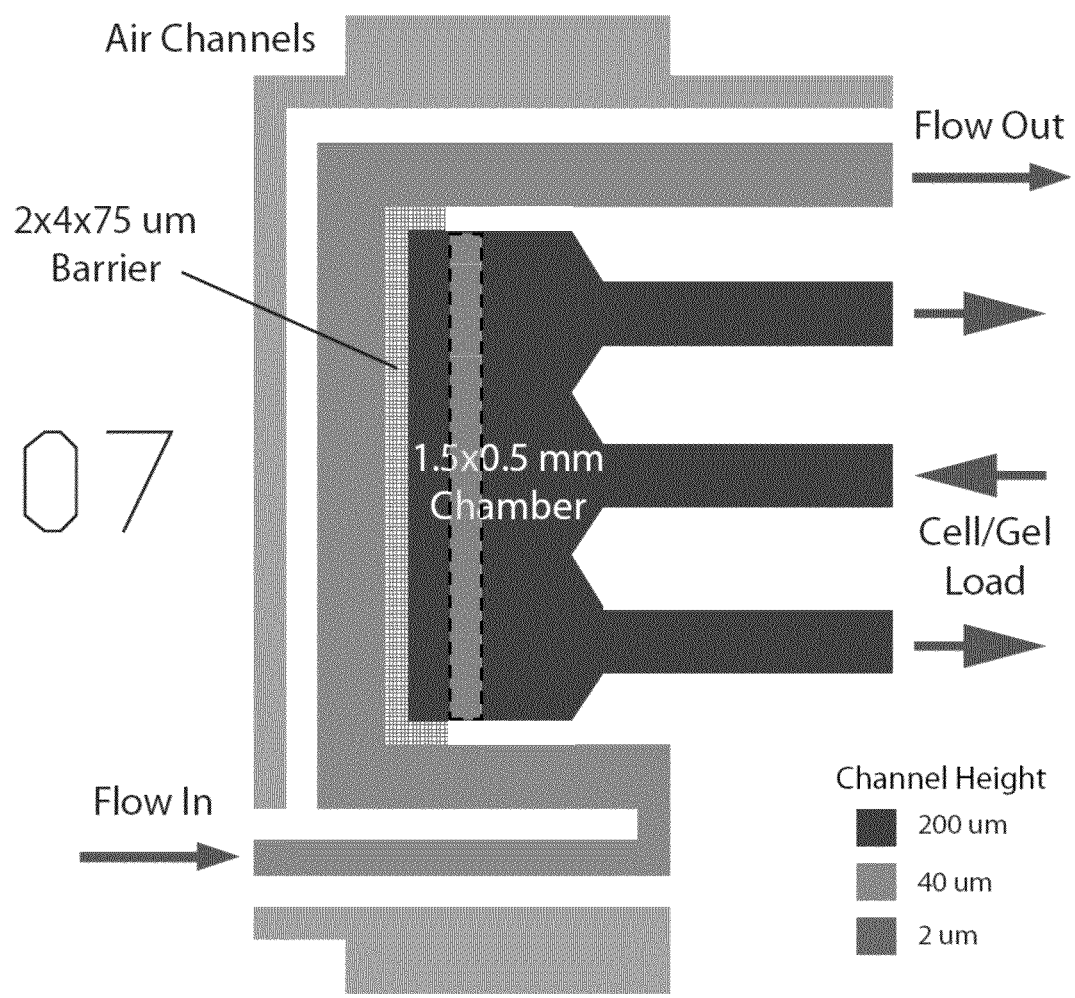

FIG. 5A-B illustrate configuration and operation of an example cell culture chamber design with multiple inlets according to specific embodiments of the invention. This example includes a cell/gel perfusion barrier with a cross-hatch perfusion passage design and an invasion barrier as discussed above. The cross hatch design allows cells in a gel matrix to be flowed into the chamber and allows for perfusion of media. While the cross-hatch perfusion barrier is presently preferred in some designs, culture chambers with different perfusion barriers or no perfusion barriers are also implemented according to specific embodiments. A flow around channel for media includes an outlet and inlet both on the same side of the barrier. FIG. 5A illustrates a general embodiment where the outlet and inlet openings are shown to the right. FIG. 5B illustrates an inlet channel to the left and outlet channel to the right, which configuration is better suited in some example systems using a well plate as described herein. This figure also provides detailed example dimensions of a sample design according to specific embodiments of the invention. Thus, in a further embodiment, a cell culture chamber is modified to allow easier culture of cells in 3D gel matrix. In this design, a perfusion barrier separates the cell culture area and the flow channel as illustrated. The barrier is designed to retain a 3D gel in the culture chamber. Coupling the barrier with the 3-channel cell/gel inlet design described above is an important feature that provides improved performance. By having separate flow inlets/outlets on each side of the barrier, it is possible to localize a fluid gel in the culture chamber, and not have it obstruct the flow channel.

An invasion barrier as described above is placed in the region indicated by the dashed line in the figure and is used to separate the cell entry and culture chamber from the invasion chamber, as will be understood from the teachings herein. In alternative embodiments, perfusion channels may be provided so that they are only adjacent to the invasion chamber.

As discussed elsewhere, in specific embodiments, the invention provides a 3D gel environment for biologic cell culture and invasion assays, for example using a temperature sensitive gel culture matrix, such as Matrigel™, Geltrex™, collagen, etc. An example gel is liquid at 4 C, which, for example polymerizes at room temperature or 37 C. In one example method, cells are initially mixed with a cell suspension on ice. The solution is then pipetted into the cell inlet well, and carried into the microfluidic chambers and the culture and invasion chambers via capillary flow. In specific examples, the plate is kept at room temperature. The flow rate allows sufficient cell/gel solution to fully fill the culture chamber prior to polymerization while the cells do not enter the invasion chamber during fluid flow because of the size of the invasion passages. The perfusion barrier prevents any of the gel solution from leaking into the flow channel. As the gel warms up, it polymerizes into a semi-solid mass, with cells embedded in the culture region. Flow of media in the flow channel diffuses into the cell culture chamber through the invasion chamber and through the gel and nourishes the cells for culture while providing an attractant for invasive cells to move through the invasion barrier to the invasion chamber. This novel design allows the invention to provide a 3D gel culture system in a microfluidic device while avoiding the problem of having gel block the flow channels.

In the example shown in FIG. 5B, the blue areas indicate air flow, and are optional and not present in all embodiments. The gray areas indicate a fluid channel, with an example height of around 40 µm, the red area indicates cell culture and invasion areas, with an example height of around 200 µm, and the green area indicates a perfusion barrier with an example height of around 2 µm. The yellow invasion barrier will generally have the same height or similar height as the culture areas (e.g., 200 µm), but will have invasion barrier structures as described above.

Once the cells are loaded, the invasion assay proceeds as outlined above, after any invasive cells have had sufficient time to move through the invasion barrier.

3D Gel System

In one example system, referred to at times herein as the 3D:M, multiplexed perfusion imaging of cells can be performed in a 3D gel matrix. An example plate contains 24 independent culture units that can be loaded with cells/gel as a user chooses. In an example system, each row of the plate (A-H) contains 3 fully independent flow units (4 wells each), consisting of a medium inlet (e.g., cols. 1, 5, 9), a cell culture/invasion/imaging well (e.g., cols. 2, 6, 10), cell/gel inlet (cols. 3, 7, 10), and an outlet (cols 4, 8, 12). Air diffusion channels (blue) provide gas transfer to the cells. The inlets are designed to allow continuous flow of culture media to the cells at 40 µl/day via a gravity driven process. In this example, each chamber is 1.5×0.5 mm in size, with a height of 200 µm. The perfusion barrier ensures uniform nutrient transfer through the gel matrix and a thin cover glass bottom (170 µm) allows for optimum image quality. An invasion barrier provides separation between a culture region and an invasion region. 3D gel loading in such a system can be performed as described above and in incorporated references.

As discussed elsewhere herein, any of the various novel microfluidic cell culture chambers and associated microfluidic structures can, according to specific embodiments of the invention, be integrated with a well titer plate device as is commonly used in macro cell culturing assays. A number of specific examples are provided below, though the invention encompasses other systems for integrating with the microfluidic devices.

In this design, each culture unit consists of 4 well positions. The first well is for perfusion medium, the second well is for cell inlet, the third well is for imaging the microfluidic chamber, and the fourth well is the outlet. A cell barrier/perfusion channel localizes cells to the cell area and improves nutrient transport during continuous perfusion culture. The low fluidic resistance of the cell inlet to outlet path enables cells to be rapidly loaded via gravity or surface tension methods without an external cell loading mechanism. The high fluidic resistance of the perfusion inlet flow channels allows long term continuous perfusion of medium via gravity flow without any external pump mechanism. An invasion barrier operates to separated cultured cells from an invasion region for invasion assays.

In an example specific system, the cell chamber is designed to mimic the interstitial tissue environment, with cells embedded or overlayed in physiologic extracellular matrix (ECM), and fed via diffusion from a continuously perfused capillary channel. The cell microenvironment enables long term growth in, e.g., a 200 micron thick gel layer. Oxygenation channels maintain adequate gas transport, and the glass coverslide bottom allows high quality cell imaging. The standard layout allows the advanced microfluidic units to be operated just like a typical 96-well plate. The gravity driven perfusion design eliminates the need for pump or tubing connections, as described above.

In an example system, an expected number of cells per unit is about 500 cells. An example perfusion rate is 40 ul/day for a single unit. The cell chamber volume is 150 mL, and the chamber dimensions are 1.5×0.5×0.2 mm. The gas diffusion membrane is 50 um silicone with a bottom surface #1.5 thickness coverglass.

An open top microfluidic cell culture chamber for continuous perfusion can also be modified with a second barrier separating an invasion region from a culture region.

6. Example Gradient Culture Chamber

Figure 6C:
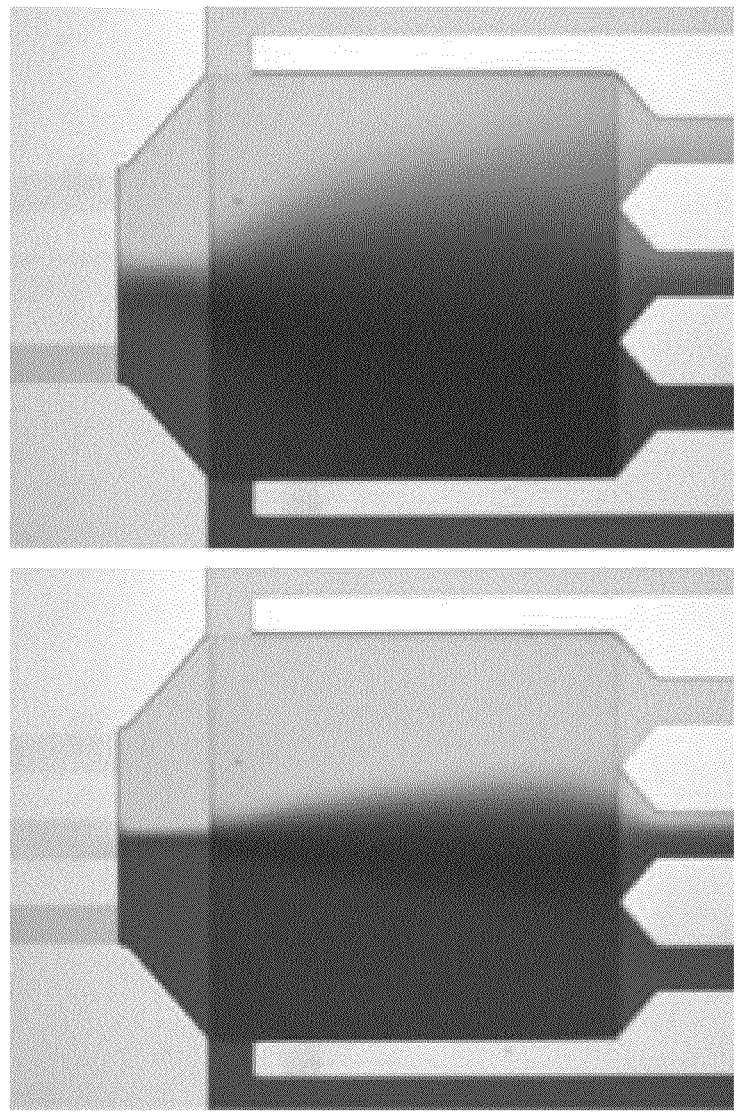

FIG. 6A-C illustrate configuration and operation of an example roughly rectangular cell culture chamber design and gradient chamber design according to specific embodiments of the invention. In the example designs, the cell culture area provided is an essentially rectangular cell culture chamber. The cell culture chamber as illustrated in FIG. 6A and FIG. 6B has cell inlet and outlet passages E2 shown at the right, and flow outlets E1 also shown at the right. In this example, the cell passages are paired, with the center pair used for cell flow loading and the pairs on either side used as a cell flow outlet. Multiple separate flow inlets are shown on the left, labeled A1, A2, B1, B2, C1, C2 and in this example design the flow inlets have a grid pattern to prevent blockage by cells. Air diffusion channels are shown surrounding the chamber. Outlet E1 provides an outlet for fluid flow that is partially isolated from the culture chamber.

FIG. 6B illustrates cell loading in a culture unit as shown in FIG. 6A. Cells are loaded via a low resistance fluidic path (with higher resistance in the flow paths). The cells are prevented from blocking the flow paths by the resistance ratio (the cells preferentially flow to the cell outlet instead of the flow channels). The channels in this particular embodiment are arranged such that the cell in and cell out channels are on the right side of the chamber. This results in the unique feature where flow of cells goes into the chamber, makes a 180 degree turn, and flows out, as illustrated by the sharply curved streamlines shown in FIG. 6B from the Cell In to Cell Out passages.). Thus, according to specific embodiments of the invention, cells are loaded (via capillary force) from the center right channel(s) and out from the top and bottom right channels. A very small amount of flow is directed towards the side outlet channels (the longer less curved streamlines shown in FIG. 6B exiting at the left edge of the chamber). The side flow is not important for cell loading, but serves to help distribute cells more evenly in the chamber. Because of the low velocity of the flow, the cells naturally settle onto the chamber floor without needing any physical barrier. The cell outlet paths help make the loading symmetric, as well as to increase the number of cells loaded into the chamber. This loading mechanism can be used to load cells, particles, beads, gels, gels with cells, etc.

FIG. 6C shows use of a design such as in FIG. 6A-B to establish a stable gradient in a cell .cell culture chamber design according to specific embodiments of the invention. The example design in FIG. 6C differs only slightly from that of FIG. 6A-B and operation modes described for one of these two designs herein apply to the other. In the FIG. 6C example, the cell passages are unpaired. Three unpaired flow inlets are shown on the left and these also have a grid pattern to prevent blockage by cells. Air diffusion channels generally are placed near the chamber, though not shown in this figure. FIG. 6C further illustrates creating a gradient in the culture chamber by flowing 2 (or more) solutions at once according to specific embodiments of the invention in the microfluidic device as described above.

7. Active Controlled Perfusion Plate

Figure 7:
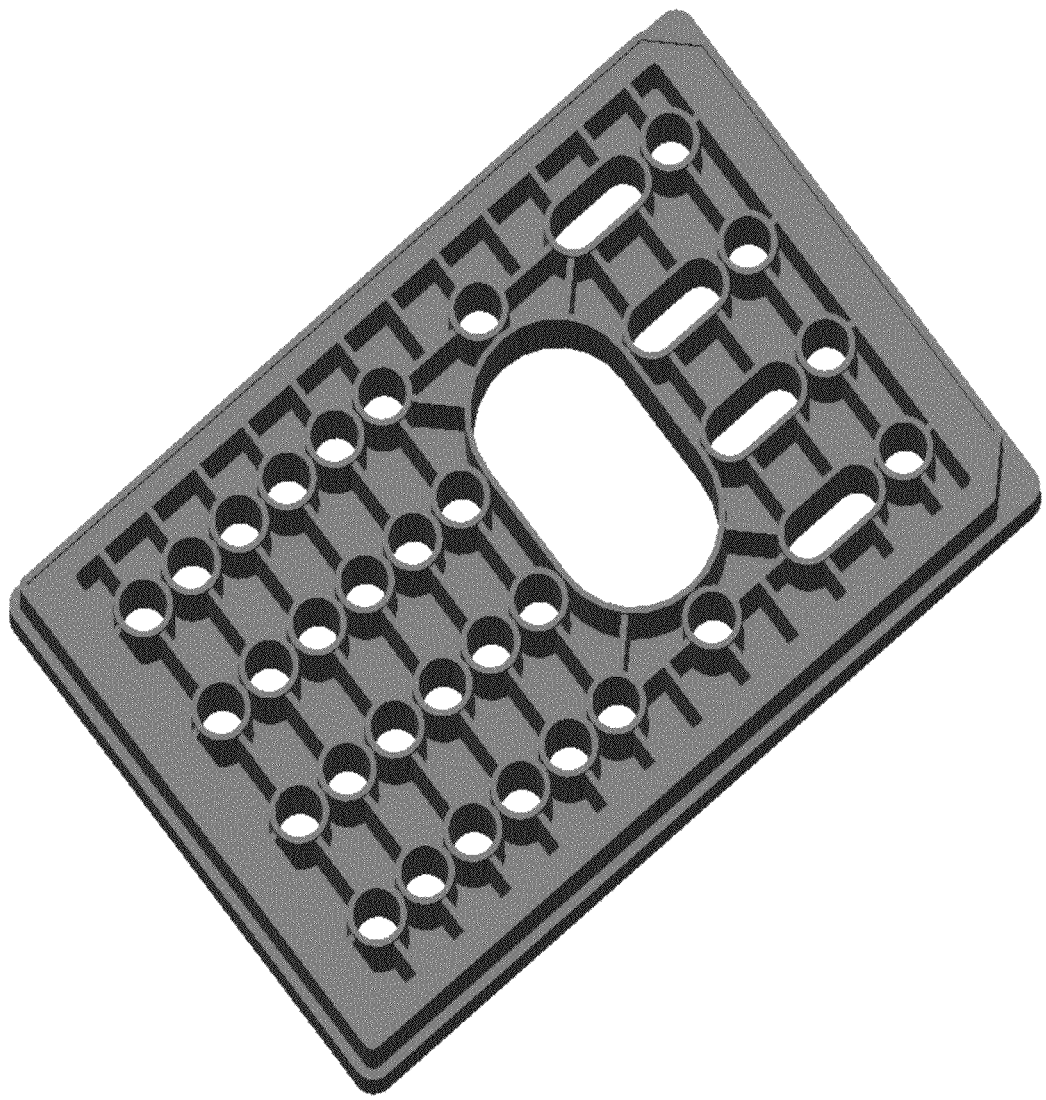
FIG. 7 illustrates a mechanical drawing of an example customized plate frame for microfluidic live cell imaging and illustrating 4 independent units (e.g., rows), a large imaging window for improved optics, air in/out ports (e.g., adjacent to the imaging window), and expanded space between the wells in this example to improve vacuum sealing of the manifold. In this example, there are 6 inlet wells per unit, with 2 outlet wells (in this example with one enlarged to house more volume).

FIG. 7 illustrates a mechanical drawing of an example customized plate frame for microfluidic live cell imaging and illustrating 4 independent units (e.g., rows), a large imaging window for improved optics, air in/out ports (e.g., adjacent to the imaging window), and expanded space between the wells in this example to improve vacuum sealing of the manifold. In this example, there are 6 inlet wells per unit, with 2 outlet wells (in this example with one enlarged to house more volume).

Figure 8:
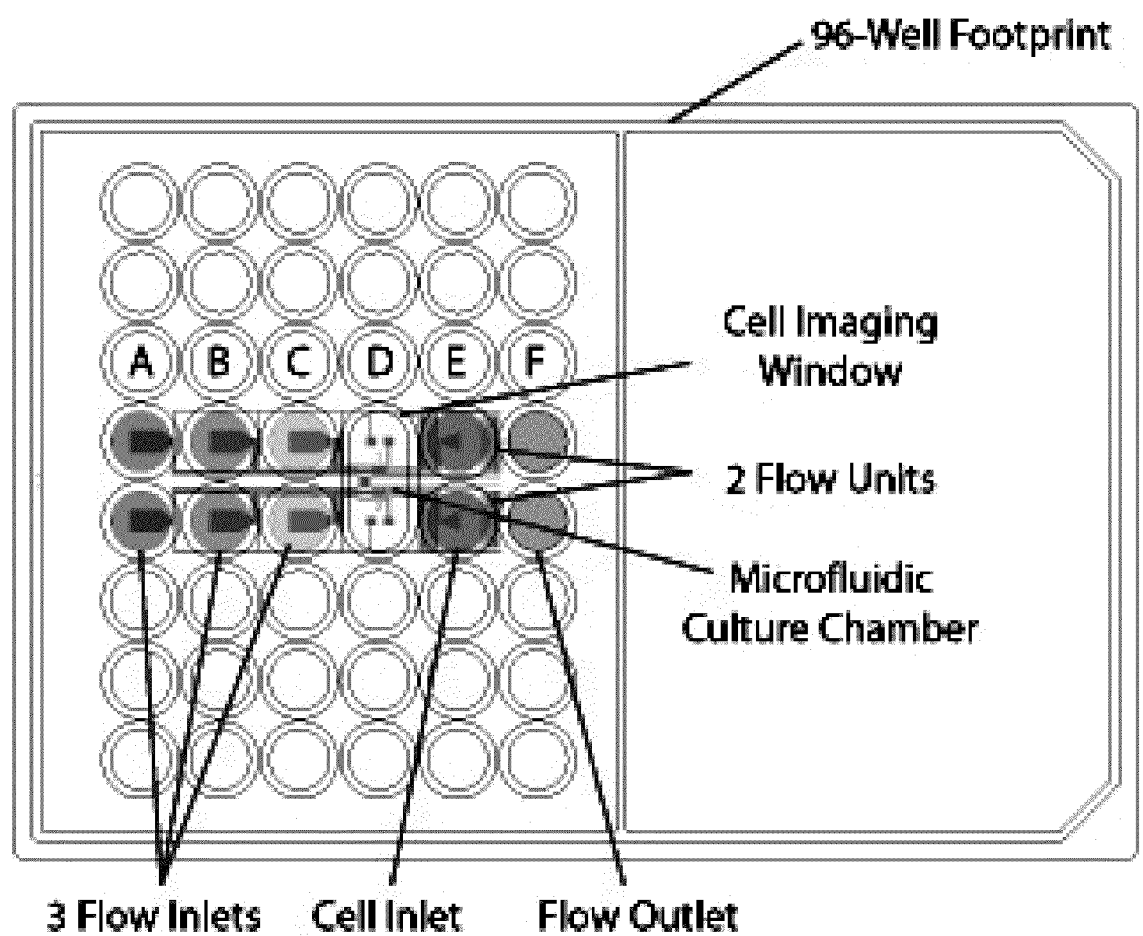
FIG. 8 illustrates a 2 culture unit plate with three flow inlets, an imaging window, a cell inlet, and a flow outlet for each unit according to specific embodiments.

FIG. 8 illustrates a 2 culture unit plate with three flow inlets, an imaging window, a cell inlet, and a flow outlet for each unit according to specific embodiments.

Figure 9:
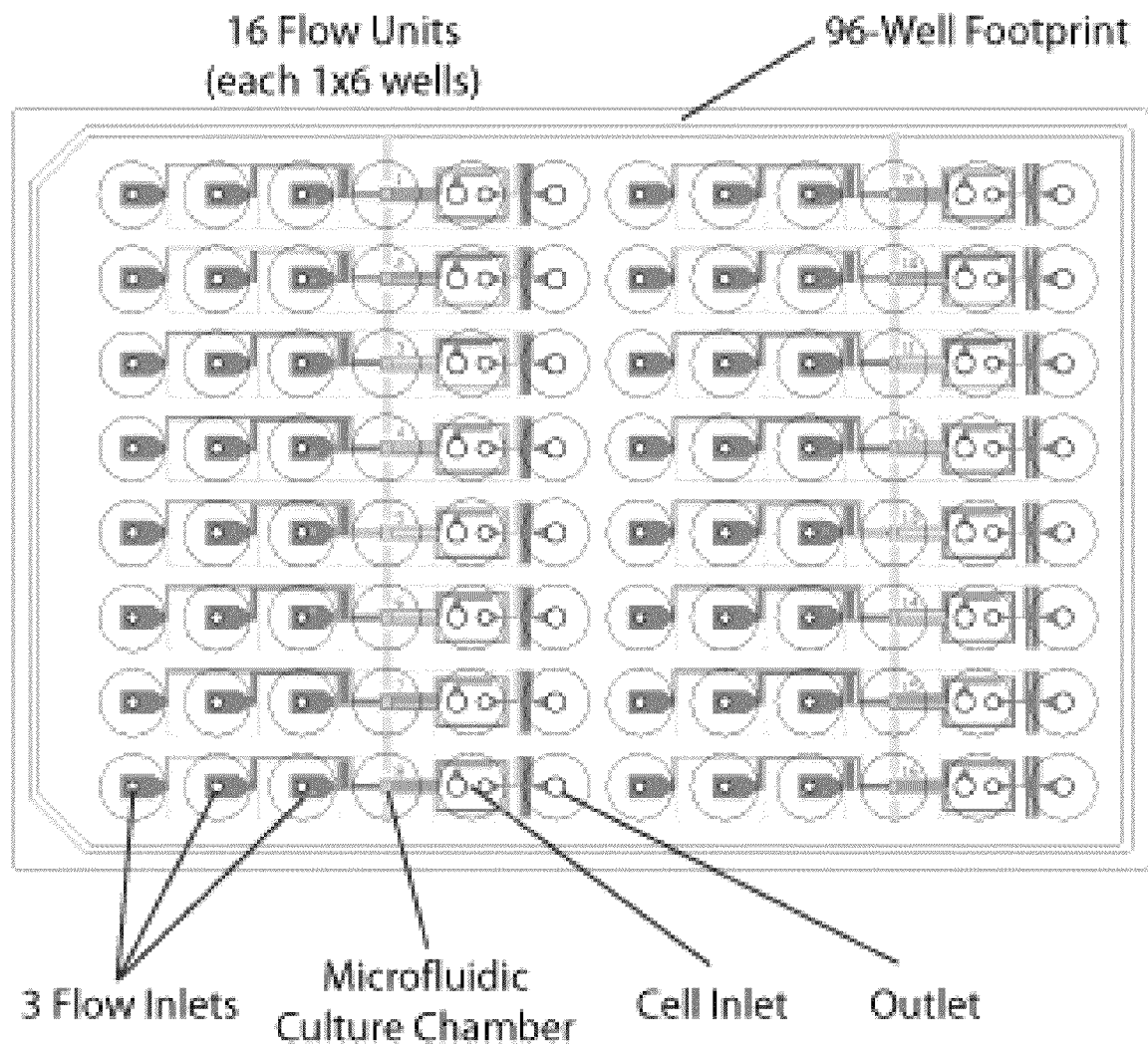
FIG. 9 illustrates a 16 unit version of a culture unit plate with three flow inlets, an imaging window, a cell inlet, and a flow outlet for each unit according to specific embodiments.

FIG. 9 illustrates a 16 unit version of a culture unit plate with three flow inlets, an imaging window, a cell inlet, and a flow outlet for each unit according to specific embodiments.

Figure 10:
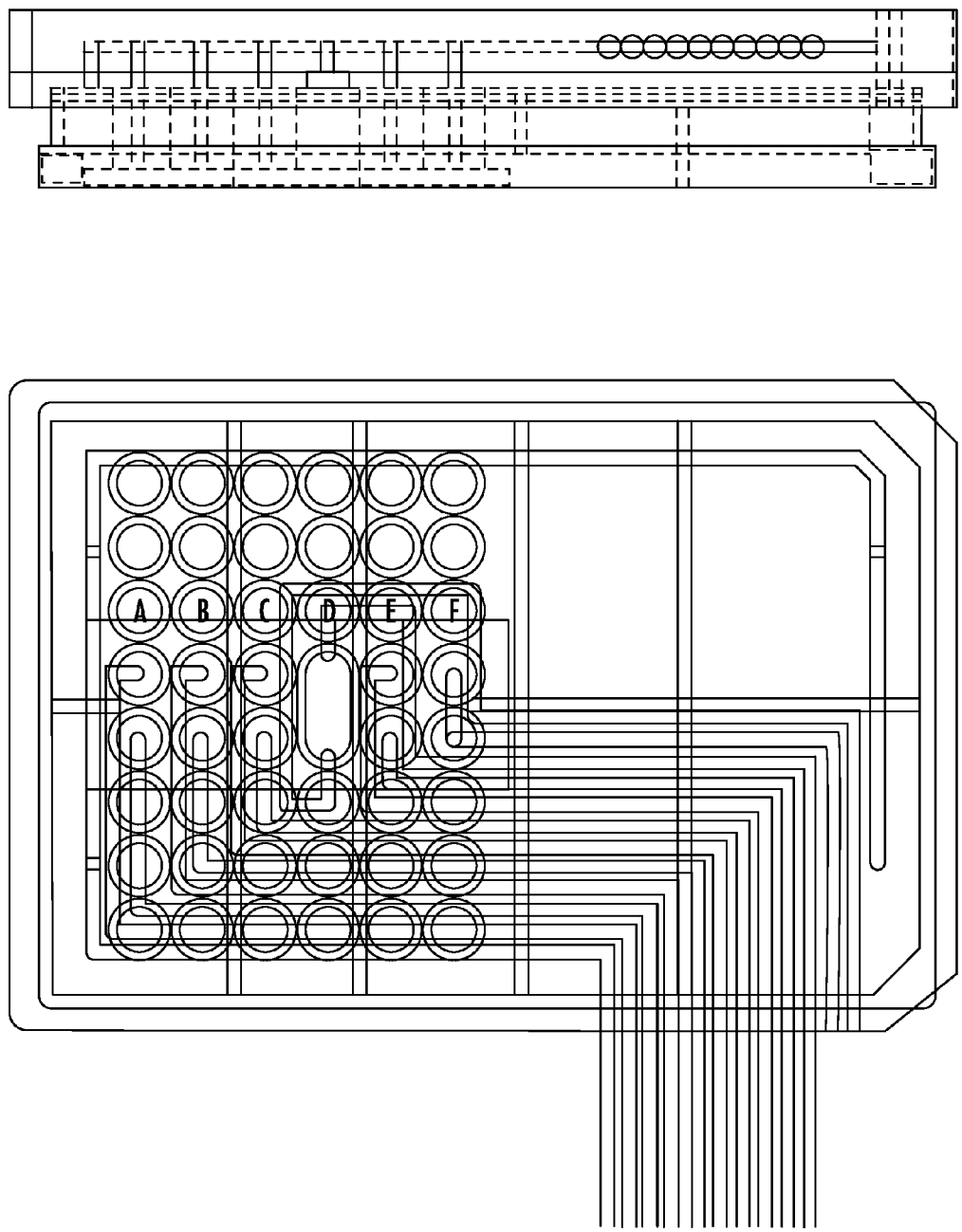
FIG. 10 illustrates a drawing of an example plate manifold with a gas perfusion line according to specific embodiments of the invention.

FIG. 10 illustrates a drawing of an example plate manifold with a gas perfusion line according to specific embodiments of the invention.

Figure 11A:
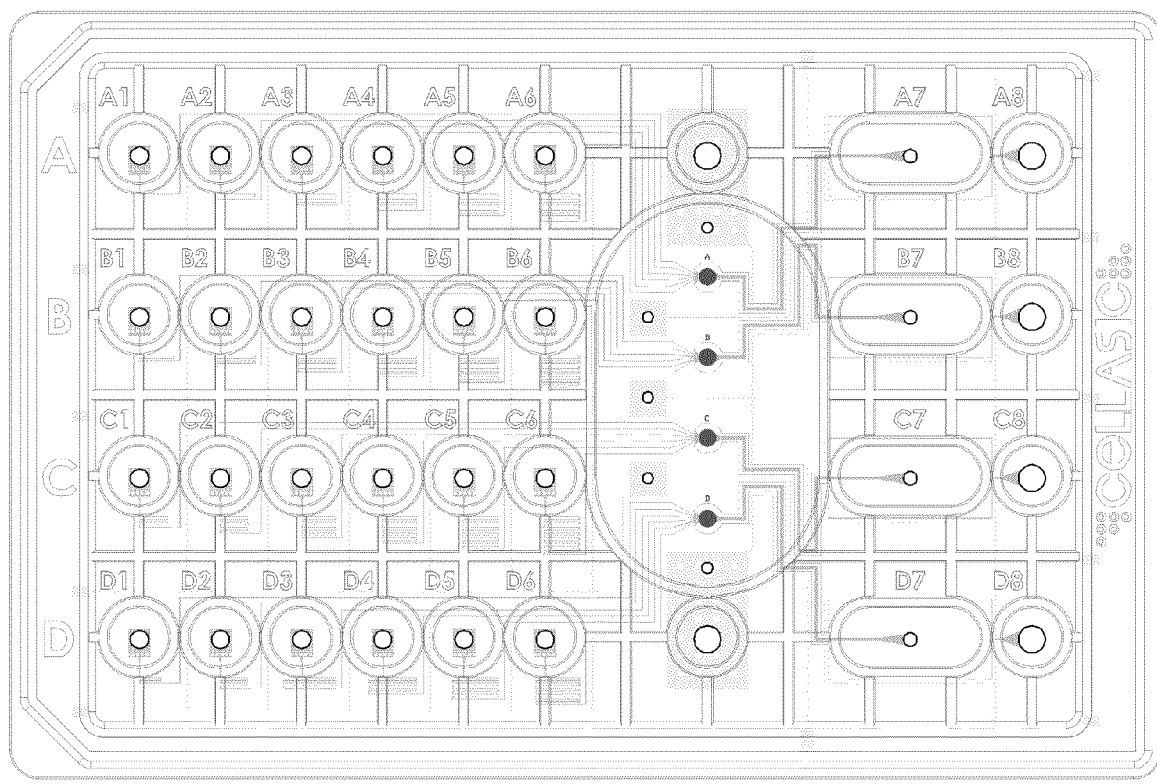
FIG. 11A-B are schematics and a photographs illustrating an example of an active control plate according to specific embodiments having four independent culture units, each having 6 flow inlets, a culture chamber and two flow outlets.
Figure 11B:
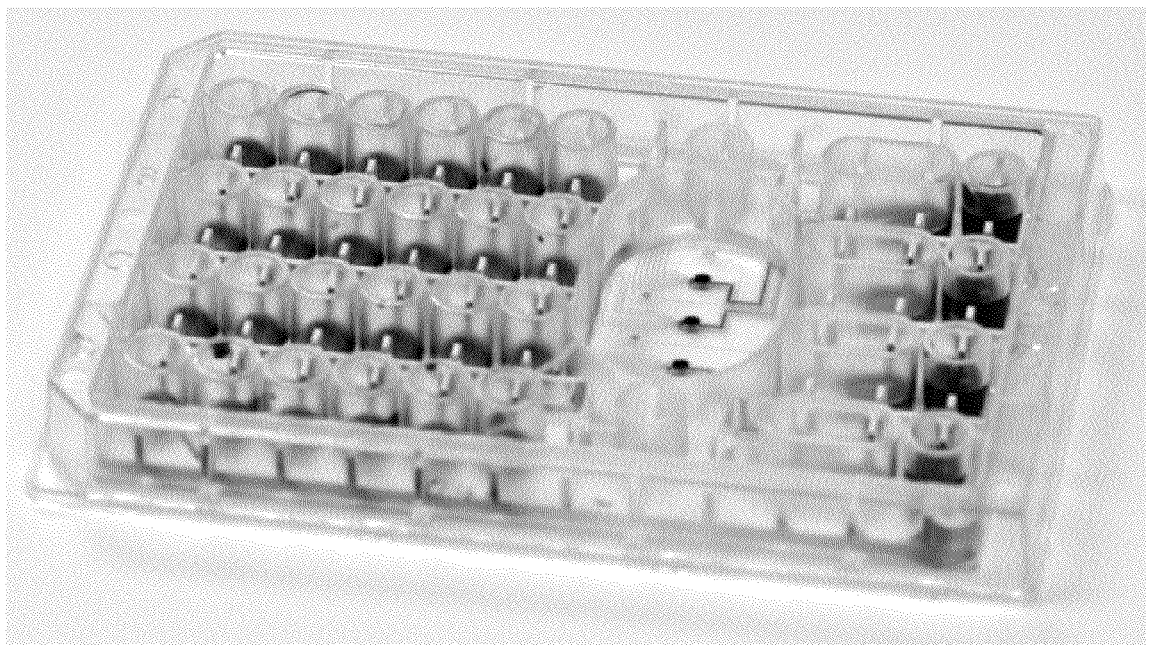

FIG. 11A-B are schematics and a photographs illustrating an example of an active control plate according to specific embodiments having four independent culture units, each having 6 flow inlets, a culture chamber and two flow outlets. FIG. 11A shows a plate design with 4 independent flow units (rows of the plate) with 6 inlet solutions, an open chamber or other culture chamber, an outlet, and a gravity flow channel. FIG. 11B shows the four open chambers (green circles), with inlet streams above and outlet streams below the open chamber. The design allows flows to pass from the inlet to outlet channels without overflowing the open chamber. The availability of multiple liquid or reagent inlets provides systems that are particularly good for live cell imaging and other experiments and assays in cell biology. In such a system a research can study cultures of pancreatic or other organ cells, or cancer cells, to determine how they respond to different drugs or other stimulus introduced via the inlets. In specific embodiments of this design, a gravity well is also provides to facilitate maintaining (e.g., feeding) the cells before experiments are performed. The plate can be sealed to a pneumatic manifold, allowing pressure driven control of the 6 inlet solutions. This allows experiments where solutions are quickly changed over the cells. Pressure driven flow of up to 10 PSI is possible due to the large resistance region between the inlet and culture chamber, leading to a pressure near the chamber less than $1/1000^{th}$ the input pressure.

The figures illustrate the layout of the active control plate with 4 independent units (rows), 6 upstream inlets (A1-A6, B1-B6, C1-C6, D1-D6), a central imaging window with four culture chambers, a large outlet well (oval, A7, B7, C7, D7), and gravity perfusion well (last column, A8, B8, C8, D8).

Figure 12A:
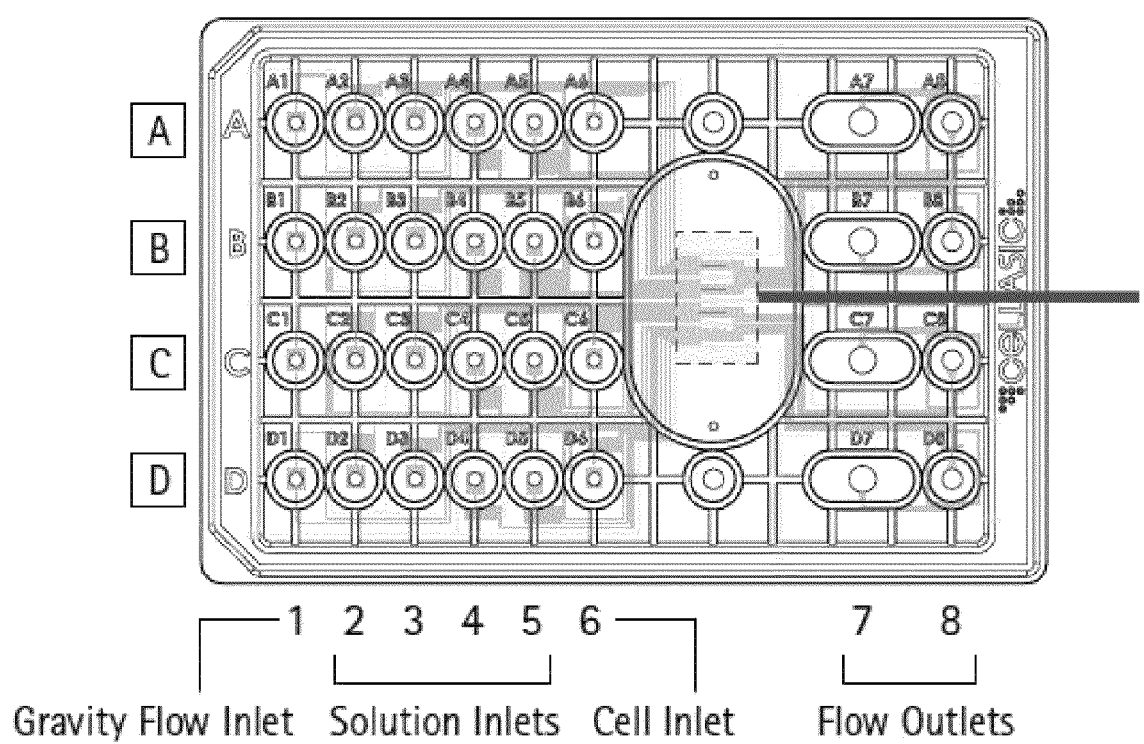
FIG. 12A-C is a diagram illustrating a further example culture plate having four independent culture units, each having 6 flow inlets, a culture chamber and two flow outlets that can be used to practice one or more methods described herein according to specific embodiments.
Figure 12B:
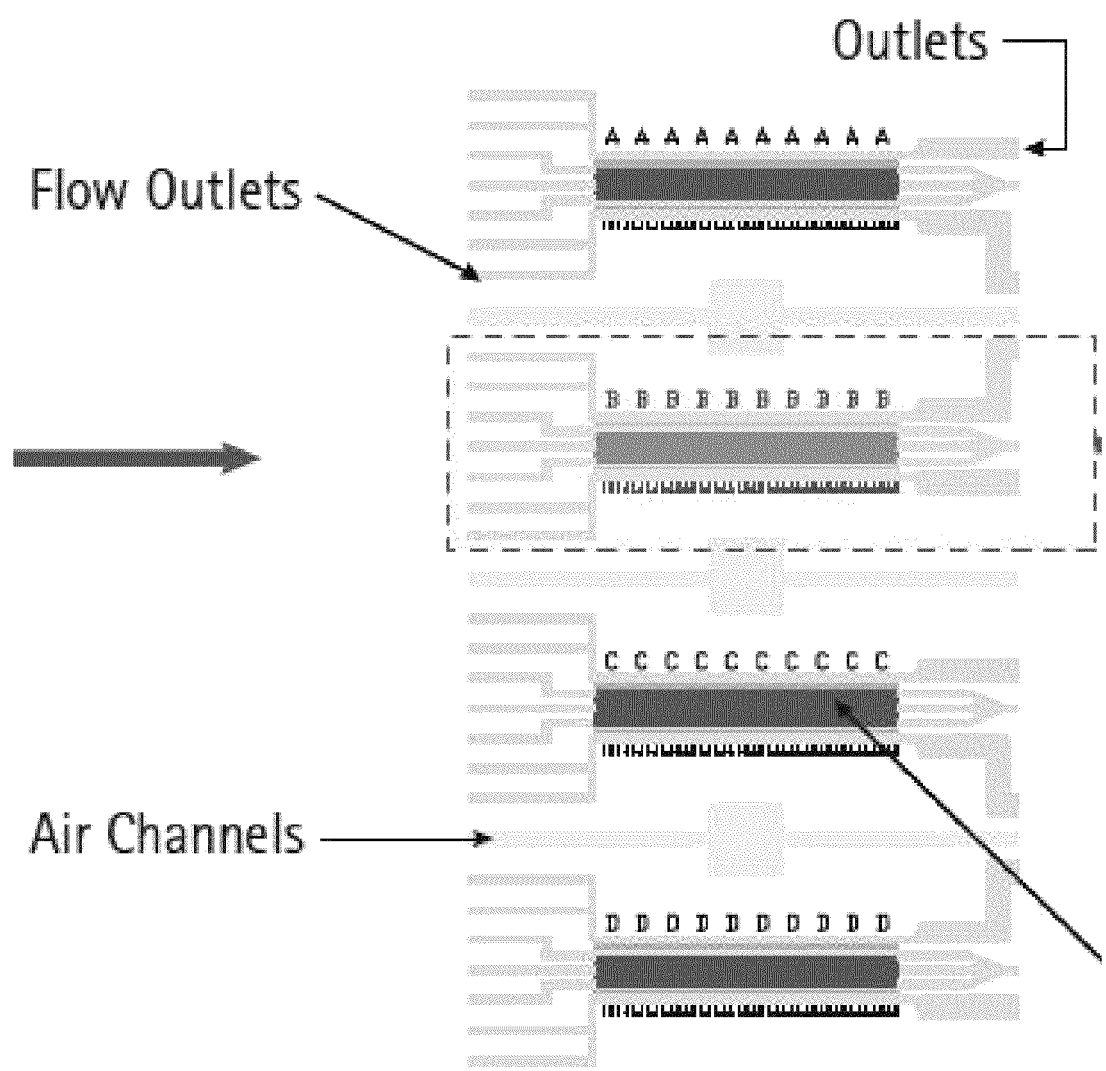
Figure 12C:
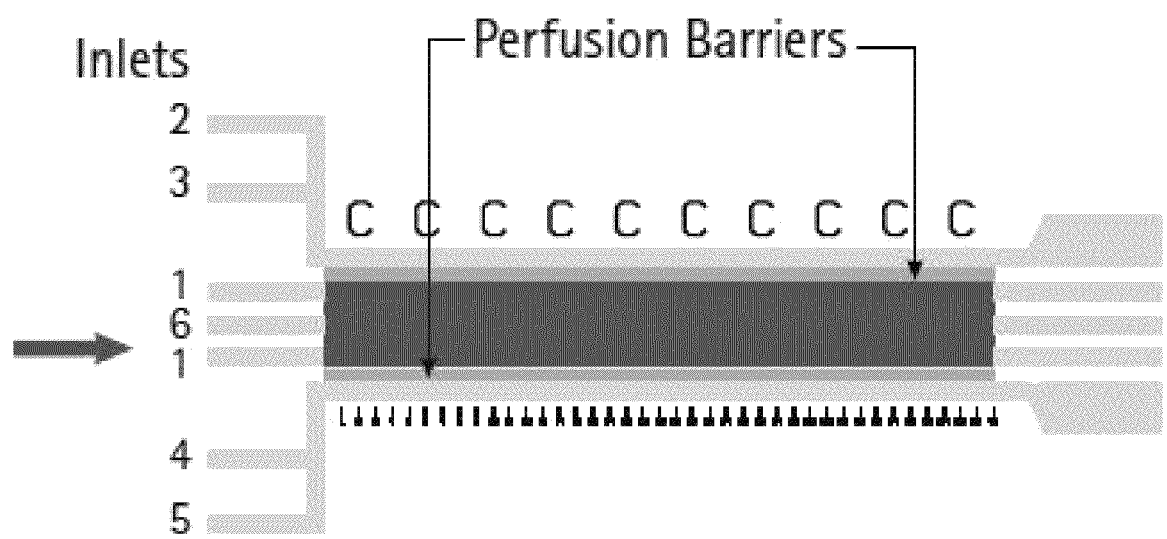

FIG. 12A-C is a diagram illustrating a further example culture plate having four independent culture units, each having 6 flow inlets, a culture chamber and two flow outlets that can be used to practice one or more methods described herein according to specific embodiments. This plate, first marketed in June 2010, has 4 independent culture chambers (for example, A-D), each with a gravity flow inlet (1), four solution inlets (2-5), a cell inlet (6), and two shared outlet wells (7 and 8). As in Each row of wells (A-D) addresses the corresponding culture chamber. (b) All four culture chambers are located under a single imaging window to minimize travel distance for high magnification phase objectives. (c) The chamber is bound by perfusion barriers on the top and bottom edges to separate the chamber from flow channels. Inlet wells 2 and 3 flow media into the upper channel, while 4 and 5 flow media through the lower channel. Gradients are established by simultaneously flowing media of different compositions through the upper and lower channels. Due to continuous perfusion, a stable gradient can be maintained for extended periods (>2 days).

8. Application Note, Cell Migration in Stable Gradient in Microfluidic Culture Device In general, cell migration is stimulated and directed by interaction of cells with the extracellular matrix (ECM), neighboring cells, or chemoattractants. During embryogenesis, cell migration participates in nearly all morphogenic processes ranging from gastrulation to neural development. In the adult organism, cell migration contributes to physiological and pathological conditions, and is central to development of therapeutics affecting wound healing and tumor metastasis. Ultimately, mechanisms of migration can be understood by analyzing cellular response to modulators (either inhibitors or activators) of migration. Therefore, techniques for the quantification and visualization of migrating cells have become central to life science research.

The most widely accepted cell migration assay is the Boyden chamber assay, using a two-chamber multi-well plate in which a membrane in each well provides a porous interface between two chambers. Chemoattractant is placed in the lower chamber, and the system is allowed to equilibrate, with the expectation that a gradient would form between the upper and lower wells. However, in reality, very steep gradients can form along a single axis perpendicular to the surface of the membrane, resulting in a lower-than-expected difference in chemoattractant concentration between upper and lower wells. As a result, this method is unsuitable for correlating specific cell responses with particular gradient characteristics (i.e., slope, concentration, temporal evolution, etc) and for studying multi-gradient signal integration. Furthermore, gradients are not very stable under "static" cell culture conditions, precluding live cell imaging.

According to specific embodiments, a cell culture chamber or system, such as shown in the above figures, can further be used to create a quantitatively defined diffusion gradient that is stable enough for long-term, live cell imaging over the course of days. Such a microfluidic gradient culture chamber of plate according to specific embodiments and methods described herein, enables precision-controlled chemoattractant diffusion across perfusion barriers to create a spatial gradient in the culture area According to specific embodiments, the flow inlets and outlets of culture chambers form a continuous-flow "infinite source/sink" that maintains a stable concentration gradient profile for days. In some of the example systems above, changes in gradient directionality, turning gradients on and off, and toggling between gradient and single solution exposure are possible.

According to further embodiments, long-term, live imaging of cells on a stable chemoattractant gradient can be used to study malignant cells or other cells capable of motility or migration. In a number of examples discussed below, the effect of a serum gradient according to specific embodiments on metastatic breast cancer cell migration distance, velocity, and degree of chemotaxis are characterized in detail.

Effect of a Serum Gradient on Metastatic Breast Cancer Cell Migration Distance, Velocity, and Degree of Chemotaxis.

In one example experiment, MDA-MB-231 (HTB-26™, ATCC®), a human breast cancer line derived from a metastatic pleural effusion site, was maintained in complete medium (Dulbecco's Modified Eagle Medium (DMEM) supplemented with 10°/ov/v fetal bovine serum (FBS), 1% non-essential amino acids, 2 mM L-glutamine and antibiotics (all EMD Millipore)) and passaged routinely by trypsinization (TrypLE™Select, GIBCO) to ensure log phase growth.

For experiments, cells were trypsinized, harvested by centrifugation, and resuspended in complete medium. 10 uL of each cell sample was mixed with 190 uL guava ViaCount® reagent (EMD Millipore) and incubated for 5 minutes at room temperature (RT). Sample data were acquired on a guava easyCyte™ HT instrument and analyzed using guava ViaCount® software (EMD Millipore).

Figure 13:
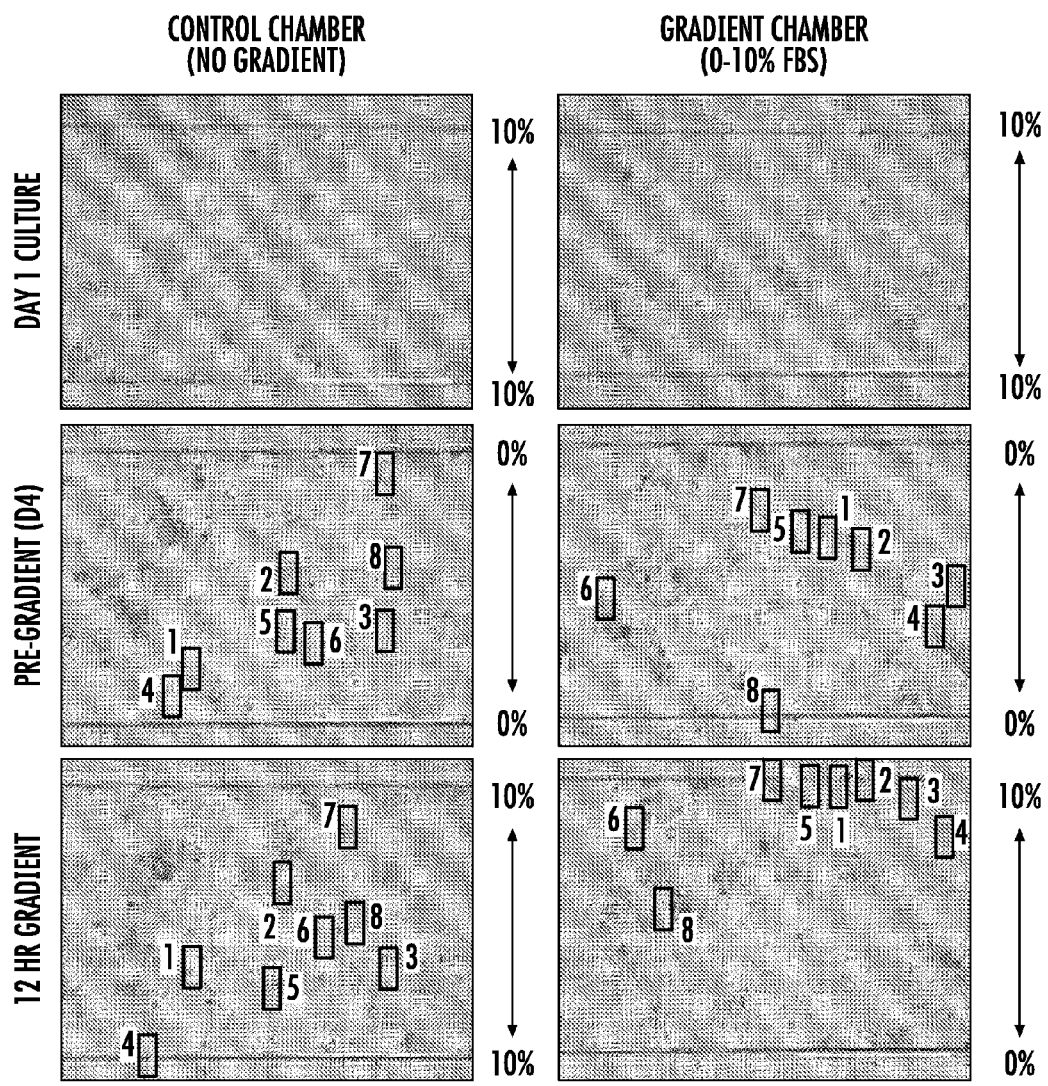
FIG. 13 illustrates one example of cell migration following exposure to a stable gradient according to specific embodiments

FIG. 13 illustrates one example of cell migration following exposure to a stable gradient according to specific embodiments In this specific example, MDA-MB-231 cell migration is shown following exposure to a stable FBS gradient using one of more of the gradient culture chambers described above. This example shows representative images (10× magnification) from cell chambers where cells were incubated in complete medium or exposed to a 0-10% FBS gradient established along the Y-axis (vertical plane). The top panel contains images captured 24 hours after cell loading. The middle panel shows cells 96 hours post-loading; the culture time is broken down into three days in complete medium followed by 24 hours of serum starvation (no FBS). It is apparent from the images that both cell expansion and movement occurred during the three-day interval. Images in the bottom panel were taken 12 hours after gradient induction.

FIG. 13 shows the migration of single MDA-MB-231 cells in response to FBS gradients over the course of three days. Both cell expansion and movement occurred during the three-day interval between the top and middle rows. Images in the bottom panel were taken 12 hours post gradient induction. In general, for those cultures exposed to a FBS gradient, there is an obvious movement of cells along the Y-axis toward the upper barrier of the cell chamber. By contrast, control cells cultured in the absence of a spatial serum gradient demonstrated less movement with far more random directional properties. The boxes (numbered 1-8) in the middle and bottom panels were used to identify particular cells and demonstrate their overall movement within the 12-hour time frame. Overall, cells exposed to FBS gradients tended to move preferentially toward the source of higher FBS concentration.

Figure 14:
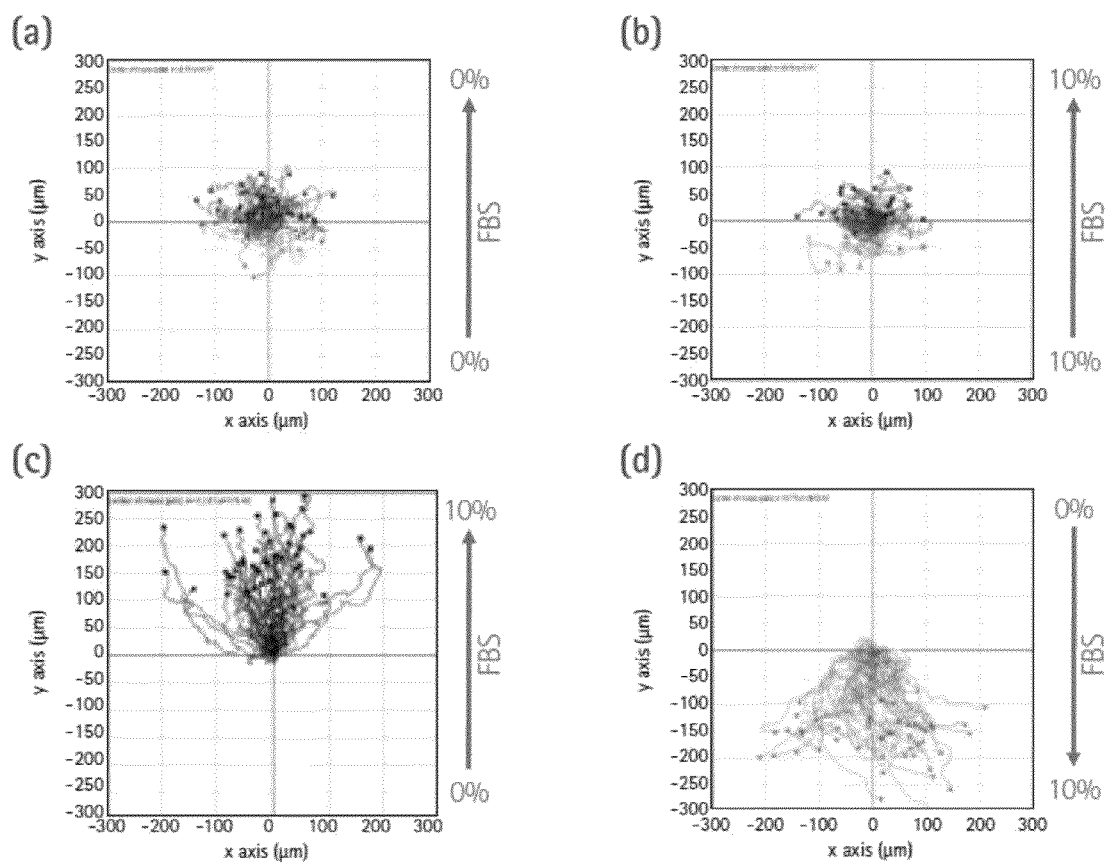
FIG. 14 illustrates as an example X/Y cellular migration plots to better illustrate the impact of a gradient on cell movement in a microfluidic cell culture device according to specific embodiments.

FIG. 14 illustrates as an example X/Y cellular migration plots to better illustrate the impact of a gradient on cell movement in a microfluidic cell culture device according to specific embodiments. In this example, the plot is an X/Y migration plots to illustrate the impact of a stable gradient in a microfluidic culture unit (e.g., an FBS gradient on MDA-MB-231) cell movement. Shown in this specific example are four plots: (a) 0/0 FBS (no gradient), (b) 10/10 FBS (no gradient), (c) 10/0 FBS (bottom to top gradient), and (d) 0/10 FBS (top to bottom gradient). For this particular example, each data set was derived from 50 representative cells from a single cell culture chamber that were tracked for the initial 36 image frames of the time-lapse video (12 hours). In each plot, Black and Red lines specify cells that possessed a net "upward" or "downward" movement relative to the Y-axis, respectively.

Image J software was used to track the migratory properties of individual cells under various culture conditions. In some of these examples, 50 cells were monitored for a total of 12 hours; the results are presented in the X/Y-plots of FIG. 14. The analysis shows that (1) cells tended to move to a far lesser degree in stable medium than when exposed to a nutrient gradient, and (2) cell migration was significantly more directed when a gradient was established within the culture chamber.

To distinguish chemotaxis toward the FBS from nondirectional migration, we analyzed movement in the x direction (perpendicular to gradient) separately from y-axis (parallel to gradient) movement (FIG. 6). Significant chemotaxis was only exhibited by cells exposed to an FBS gradient (10/0 FBS A-C and 0/10 FBS). Cells in a spatially-constant FBS culture demonstrated very little overall movement.

Figure 15:
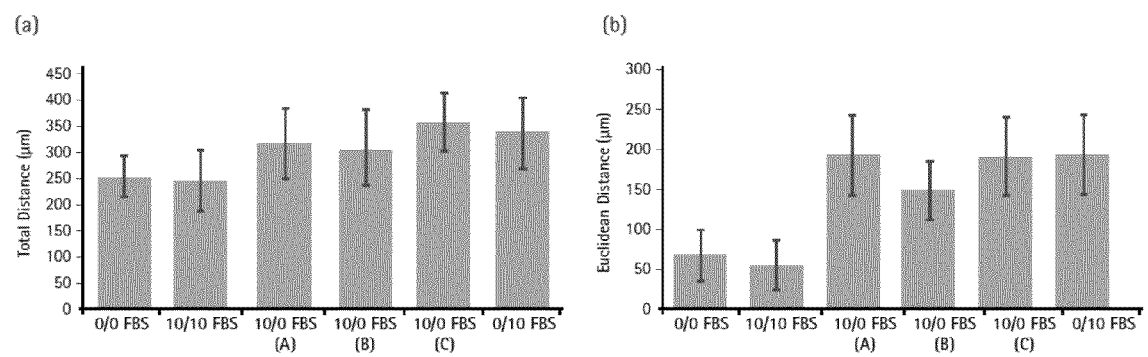
FIG. 15 illustrates as an example cell migration as function of distance traveled in a microfluidic cell culture device according to specific embodiments.

FIG. 15 illustrates as an example cell migration as function of distance traveled in a microfluidic cell culture device according to specific embodiments. In this example, MDA-MB-231 cell migration as function of distance traveled is shown. For each of the six conditions (n=50 representative cells for each), the mean distance migrated (in µm) was measured as a function of total (a) and Euclidean distance (b), where the latter represents a straight line from starting to end position.

Using the migration distances calculated from the migration plots, total migration distance and Euclidean distance with respect to gradient conditions are shown in FIG. 15A. As shown, there was a small increase in the overall distance traveled for gradient cultures as compared to cells in stable environments. Interestingly, there was little difference between 0/0 (serum-starved) and 10/10 (complete medium) conditions. By contrast, a large difference was found between the two conditions (stable vs. gradient) when net (Euclidean) distance was assessed FIG. 15B. In this case, cells exposed to an FBS gradient migrated more than 3-fold farther away from their site of origin than those cells in a constant media state. Such findings suggest the cells are actively seeking the nutrient-rich media at the high FBS concentration end of the gradient, and therefore exhibit a greater degree of directional migration.

Figure 16:
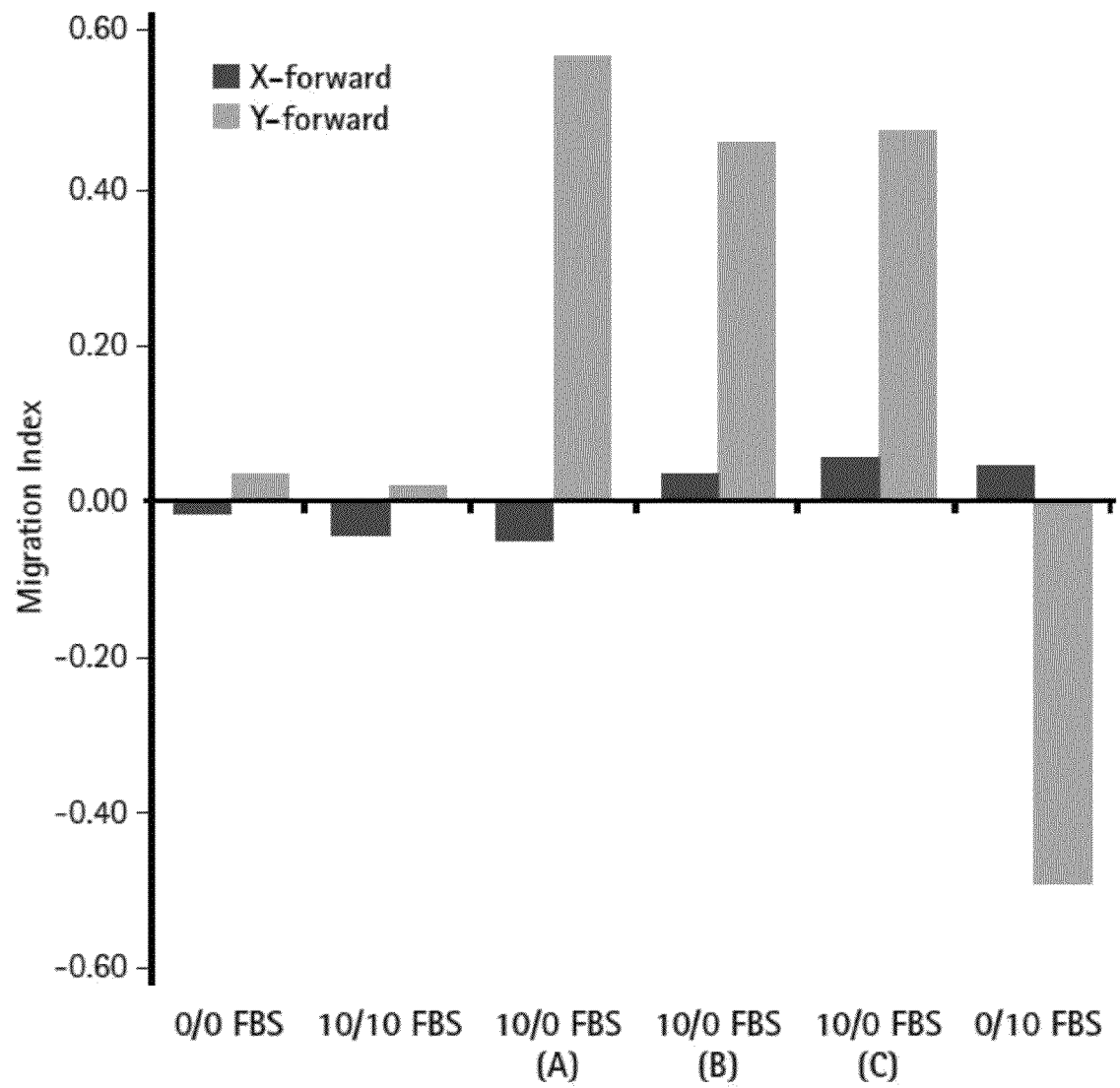
FIG. 16 illustrates as an example a plot showing cells exposed to stable gradients in a microfluidic cell culture device move faster than those in stable media environments according to specific embodiments.

FIG. 16 illustrates as an example a plot showing cells exposed to stable gradients in a microfluidic cell culture device move faster than those in stable media environments according to specific embodiments. This example shows that in some cases, cells exposed to gradients (e.g., FBS) move faster than those in stable media environments. This graph demonstrates the difference in migration velocity (μm/min) among the four culture conditions in this example. Velocities were calculated based on mean total distance migrated.

In general, cells migrated with a slightly higher velocity in chambers where an FBS gradient was established. Of note, the migrating cells in one of the four gradient cultures (10/0 FBS (Q) exhibited far greater migration velocity than the other examples. From observations made during this experiment, there are two factors which may potentially contribute to accelerated cell migration: (1) cells tended to migrate farther in cultures of lower cell density, and (2) members of a cell cluster tended to migrate faster than isolated counterparts. This latter response is potentially caused by localized cell-cell communication within the microenvironment, as previously reported in studies analyzing the relationship between cell-cell interactions and migration rate.

Figure 17:
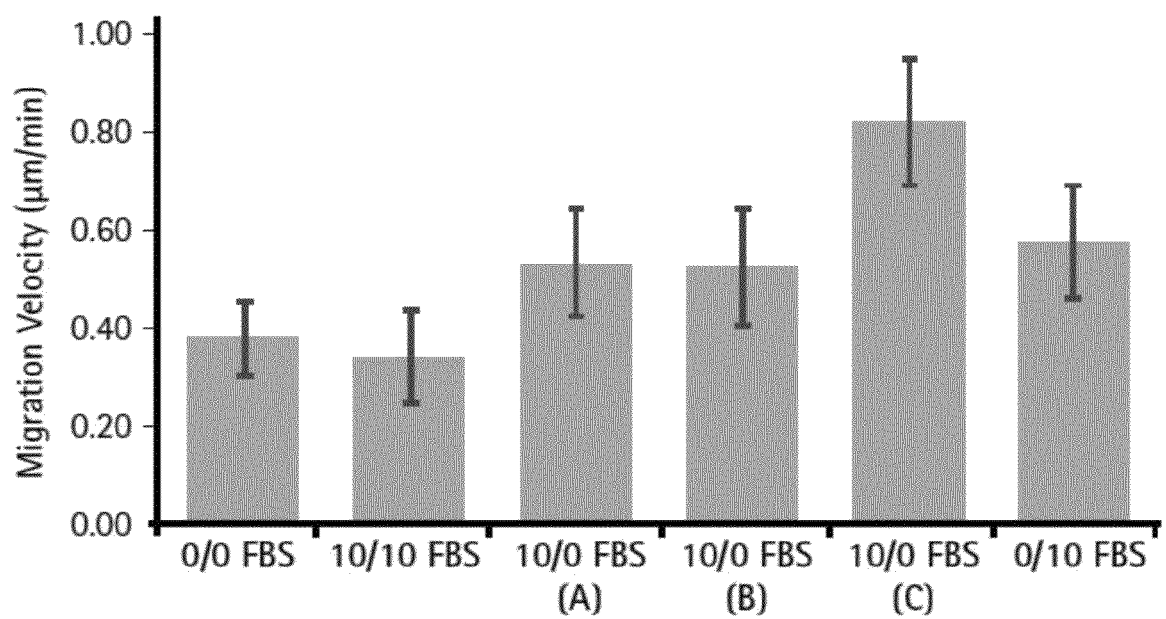
FIG. 17 illustrates one example showing that exposure to gradients stimulated active migration of cells towards a high concentration sink according to specific embodiments.

FIG. 17 illustrates one example showing that exposure to gradients stimulated active migration of cells towards a high concentration sink according to specific embodiments. In this example, exposure to FBS gradients stimulated active migration of MDAMB-231 cells towards the high concentration sink. The migration index provides a measurement of the movement of cells (relative to their position of origin) in both the X (perpendicular to the gradient) and Y (parallel with the gradient) directions. For each of the six assays, both values for both planar movements are displayed (each bar represents the mean of 50 individually-tracked cells within a single cell chamber).

Example Set Up

Prior to the specific experiments described above, ambient temperature within the cell culture chamber was calibrated to 37° C. using the CellASIC™ ONIX Microincubator Controller, Temperature Calibration Plate and DirecTemp™ temperature monitoring software (EMD Millipore). Cell chambers were primed using phosphate-buffered saline (PBS) solution that was aspirated from wells 1, 6, 7 and 8 of the CellASIC™ plate and 10 uL culture media was pipetted into well 6. The procedure was repeated for all chamber units on the microplate. The plate was vacuum-sealed to the F84 Manifold. Using the CellASIC™ ONIX FG software, medium was set to perfuse from well 6 at 0.25 psi for 2 minutes.

For Cell Loading, trypsinized MDA-MB-231 cells were resuspended at $2 \times 10^6$/mL in complete medium. Medium was aspirated from the PTFE ring in wells 1 and 6. Well 1 was replaced with 10 uL medium and well 6 was replaced with 10 uL of cell suspension. The plate was vacuum-sealed to the F84 Manifold and placed on the stage of an EVOS™fl inverted microscope (Advanced Microscopy Group) to monitor the loading process. Cells were loaded by simultaneously flowing from wells 1 and 6 at 0.4 psi for 0.3 minutes (18 seconds) using the CellASIC™ ONIX FG software. Plates were placed in a standard 37 #C/5% $CO_2$ incubator for one hour to allow for cell attachment prior to automated media perfusion.

For these example experiments, each involved three distinct phases—complete media feeding (from inlet wells 2 and 4, flowing at 1 psi for 48 hours), serum starvation (from inlet wells 3 and 5 flowing at 1 psi for 24 hours) and exposure to a 0-10% FBS gradient To establish a gradient within the culture chamber, 300 uL complete medium and complete medium minus FBS were loaded into inlet wells 2 and 4, respectively, and flowed simultaneously at 1 psi. In certain instances, after 24 hours, the gradient's orientation was reversed by switching the source wells for perfusion. In this case, complete medium minus FBS and complete medium were loaded into wells 3 and 5, respectively, and flowed simultaneously at 1 psi. Media perfusion in this system was accomplished using the CellASIC™ ONIX microfluidic system.

Images were captured using the EVOS™fl inverted microscope at 10× magnification. Time-lapse imaging was performed during the FBS gradient portion of each experiment; images were captured at 20-minute intervals for the length of the gradient exposure time. Images from MDA-MB-231 cell migration assays were analyzed using Image J software (NIH) in combination with Manual Tracking (NIH) and Chemotaxis tool (ibid.) plug-ins. In each case, 50 representative cells were tracked for migratory properties across a sequential series of 36 images (12 hours in culture).

The experiments demonstrated that real-time live cell imaging during highly controlled cell migration studies can be used to observe and study the cellular processes of migration and invasion that are involved in mechanisms underlying pathological phenomena such as wound healing and tumor metastasis.

9. Pneumatic Manifold

While gravity or passive loading is effective for some microfluidic cell culture devices and desirable in some embodiments, a proprietary pneumatic manifold, as described herein and in the above referenced applications may be mated to the plate and pneumatic pressure is applied to the cell inlet area for cell loading and for culturing during invasion assays.

According to further embodiments of the invention, a novel cell loading system uses a pneumatic manifold and pneumatic pressure to place cells in the micro culture area. With the addition of this cell loading system, microfluidic cell culture and analysis can be fully automated using other automated equipment that exists for handling standard titer plates.

In further embodiments, the invention involves a microfluidic system to allow control of the cell culture environment for long-term time-lapse microscopy of adherent cells. As the trend towards "systems biology" continues, it will become increasingly important to study dynamic behavior in individual live cells as well as to improve the functionality and economics of high throughput live cell screening. According to specific embodiments of the invention, the invention provides a multiplexed microfluidic flow chamber allowing for time-lapse microscopy experimentation among other assays. The microfluidic chamber uses an artificial endothelial barrier to separate cells from flow channels. The device is formatted to a standard well plate, allowing liquid and cell samples to be directly pipetted into the appropriate inlet reservoirs using standard equipment. A custom pneumatic flow controller is then used to load the cells into the culture regions as well as to switch between different exposure solutions. A digital software interface can be used to allow a user to program specific inputs (pulses, ramps, etc.) over time to expose the cells to complex functions during time-lapse imaging.

Dynamic responses in living cells are the foundation for phenomena such as biological signal processing, gene expression regulation, differentiation, and cell division. In specific embodiments, the invention involves a system capable of controlling the cellular micro-environment in a multiplexed format compatible with current cell culture methods. Cell response can be quantified using high magnification fluorescence microscopy to derive kinetic information with sub-cellular resolution. This capability has broad applications in cellular systems.

Figure 18A:
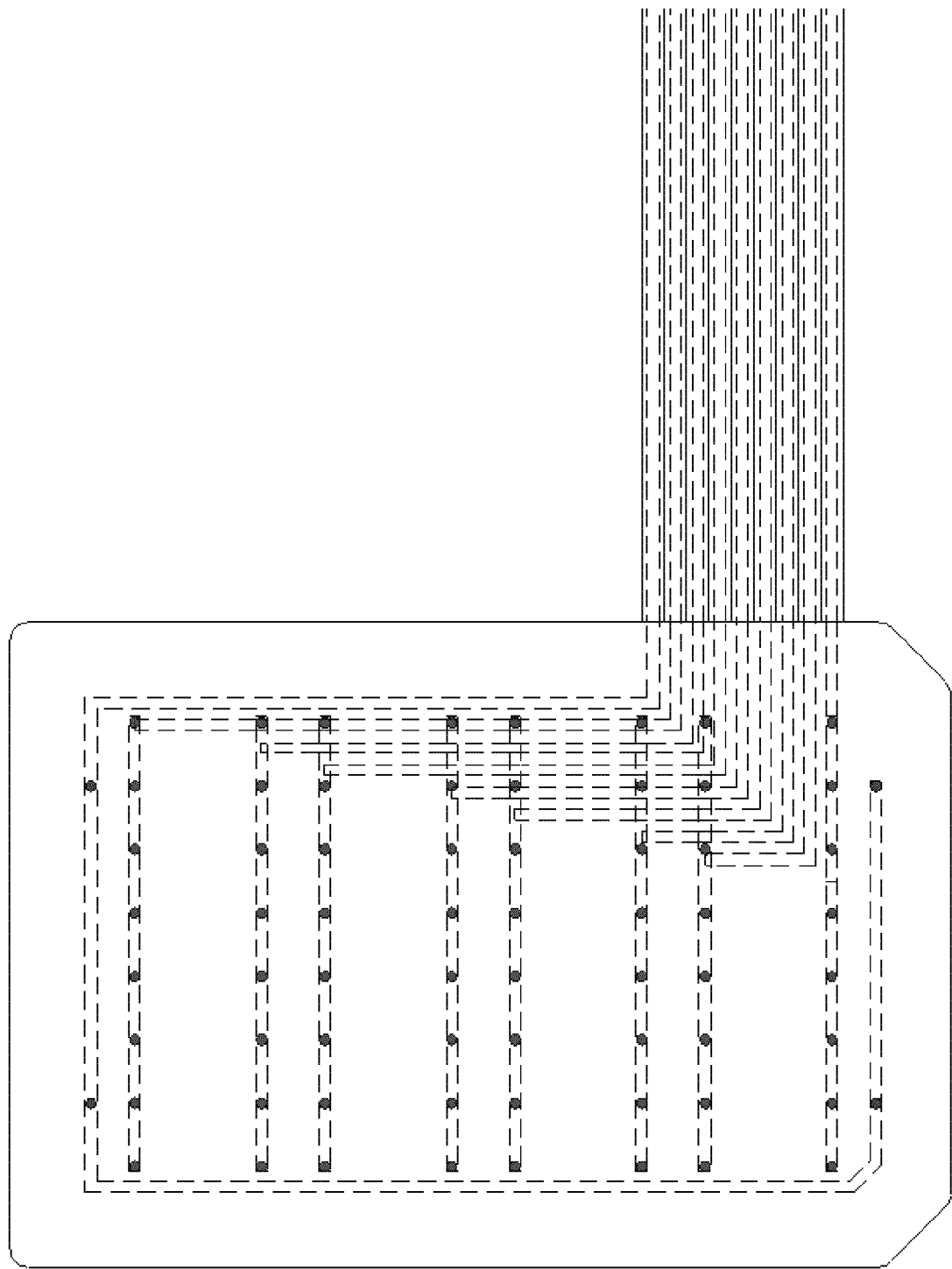
FIG. 18A-C shows a top view, side view, and plan view of a schematic of an example manifold according to specific embodiments of the invention. In this example, the eight tubing lines to the right are for compressed air, and each is configured to provide pressure to a column of cell inlet wells in a microfluidic array. The left-most line in the figure is for vacuum and connects to an outer vacuum ring around the manifold. Each column of wells is generally connected to a single pressure line with wells above imaging regions skipped.
Figure 18B:
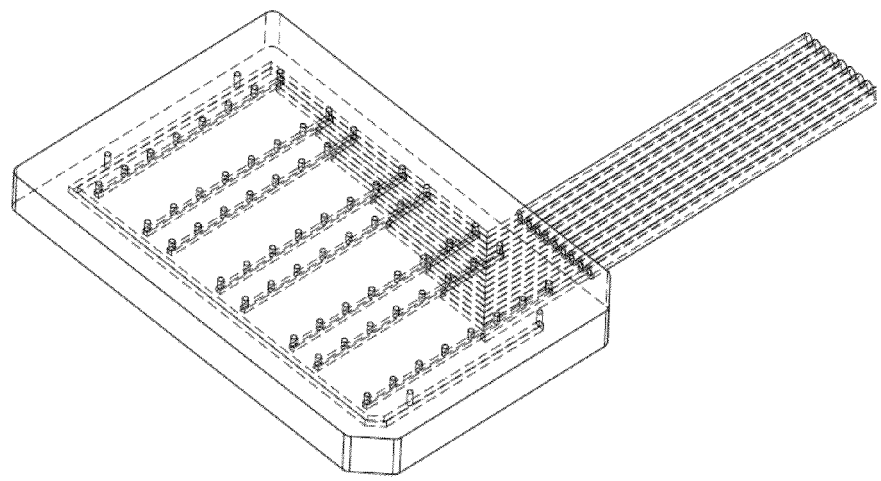
Figure 18C:
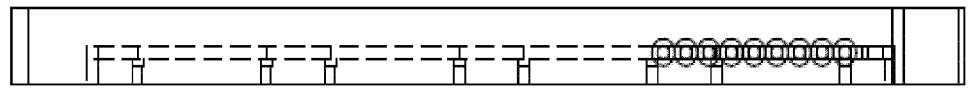

FIG. 18A-C shows a top view, side view, and plan view of a schematic of an example manifold according to specific embodiments of the invention. In this example, the eight tubing lines to the right are for compressed air, and each is configured to provide pressure to a column of cell inlet wells in a microfluidic array. The left-most line in the figure is for vacuum and connects to an outer vacuum ring around the manifold. Each column of wells is generally connected to a single pressure line with wells above imaging regions skipped. The manifold is placed on top of a standard well plate or other configuration of plate. A rubber gasket lies between the plate and manifold, with holes matching the manifold (not shown). The vacuum line creates a vacuum in the cavities between the wells, holding the plate and manifold together. Pressure is applied to the wells to drive liquid into the microfluidic channels (not shown). A typical pressure of 1 psi is used, therefore the vacuum strength is sufficient to maintain an air-tight seal. In one example there are 9 tubing lines to the pressure controller: 8 lines are for compressed air and 1 line is for vacuum (leftmost). In specific example embodiments, each column is connected to a single pressure line. Columns above the cell imaging regions are skipped.

Pressurized cell loading in a system according to specific embodiments of the invention has been found to be particularly effective in preparing cultures of aggregating cells (e.g., solid tumor, liver, muscle, etc.). Pressurized cell loading also allows structures with elongated culture regions to be effectively loaded. Use of a pressurized manifold for cell loading and passive flow for perfusion operations and invasion assay allows the invention to utilize a fairly simple two inlet design, without the need for additional inlet wells and/or valves as used in other designs.

Modified Manifold

In a further embodiment, a plate manifold includes an additional "gas line" that is used to bathe the cells in the microfluidic device with a specified gas environment (for example, 5% $CO_2$). Other examples include oxygen and nitrogen control, but any gaseous mixture can be sent to the cells. The gas flows through the manifold into the sealed wells above the cell culture area and holes in the microfluidic device enable the gas to flow into specified microfluidic air channels, as described above. The gas permeable device layer (PDMS) allows the gas to diffuse into the culture medium prior to exposing the cells. By continuously flowing the gas through the microfluidic plate, a stable gas environment is maintained.

This provides an optional means for controlling the gas environment to placing the microfluidic plate into an incubator. In this modified manifold, the manifold can be used to create a "micro-incubator" independent of the ambient air.

Figure 19:
FIG. 19 illustrates an example system and manifold for operating the microfluidic plates according to specific embodiments of the invention.
Figure 20:
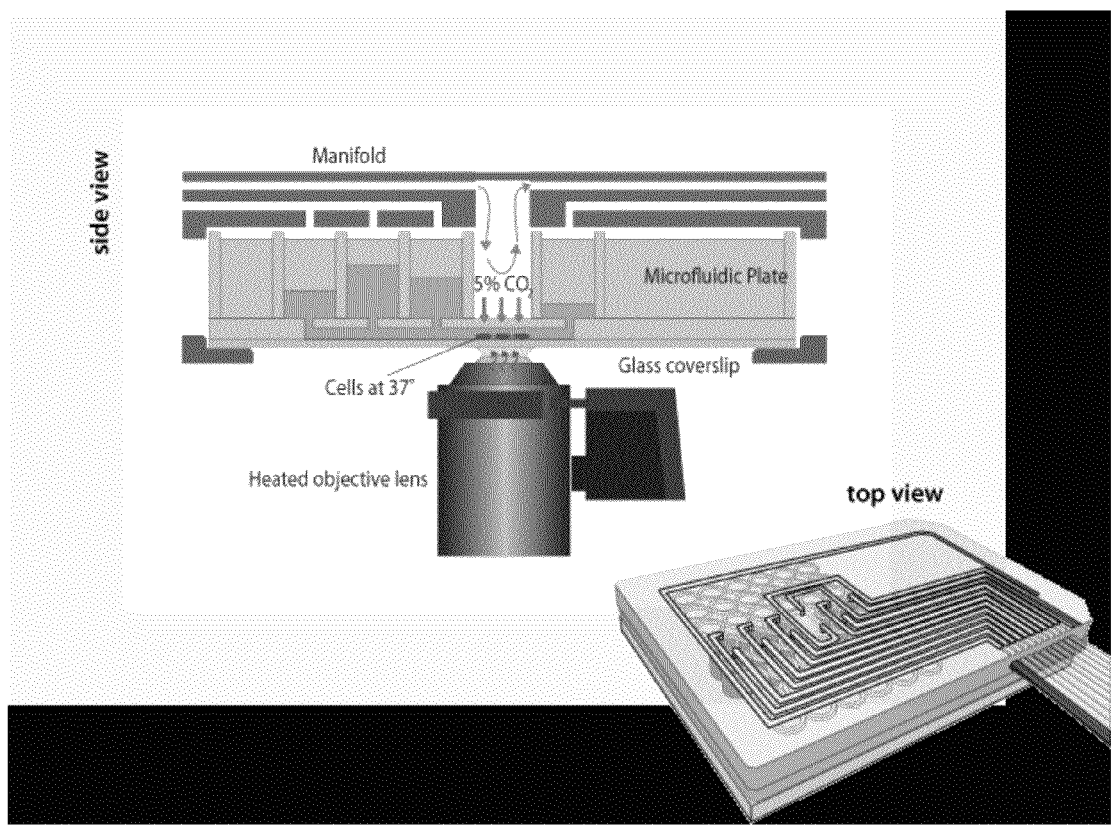
FIG. 20 illustrates a manifold with additional gas line and an objective lens and showing five active wells in a microfluidic plate connected to a culture device according to specific embodiments of the invention.

FIG. 19 illustrates an example system and manifold for operating the microfluidic plates according to specific embodiments of the invention.

10. Automated Systems

Because the plates are designed to be handled using SBS compliant instruments, various "off-the-shelf" machines can be used to create an automated system. This schematic shows an example of how this is accomplished. A robotic arm (plate handler) moves the microfluidic plates from station to station. An automated incubator stores the plates at the proper temperature and gas environment for long term perfusion via gravity flow. The pipettor dispenses liquids (media, drugs, assay reagents, etc.) to the inlet wells and removes liquid from the outlet wells. A plate reader is used for assay. The cell loader is optionally used to introduce the cells to the microfluidic arrays at the beginning of the experiment. The cell loader in particular is generally not "off-the-shelf" and operates by applying pneumatic pressure to specified wells of the array plate to induce flow. Standard or custom computer software is available to integrate operations.

The basic process includes: 1) removing the plate from the incubator, 2) removing liquid from the outlet wells via the pipettor, 3) moving a media/drug storage plate from the "plate stacks," 4) transferring liquid from the media/drug plate to the microfluidic plate via the pipettor, 5) placing the microfluidic plate into the incubator, 6) repeat for each plate, 7) repeat after specified time interval (e.g. 24 hours).

The 96-well plate standard allows the microfluidic system to be operated using standard techniques and equipment. For example, liquid dispensing is achieved with standard pipette mechanics, and cell culture and analysis is compatible with existing incubators and plate readers. A custom built cell loading system can be used to load the cells using air pressure as described above. The gravity driven flow culture configuration utilizes the medium level difference between the inlet and outlet well as well as engineering the fluidic resistances to achieve the desirable flow rate in nL/min regime. This provides the significant advantage of being able to "passively" flow culture medium for long periods of time (for example, up to 4 days) without the use of bulky external pumps.

Integrated Systems

Integrated systems for the collection and analysis of cellular and other data as well as for the compilation, storage and access of the databases of the invention, typically include a digital computer with software including an instruction set for sequence searching and/or analysis, and, optionally, one or more of high-throughput sample control software, image analysis software, collected data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises valves, concentration gradients, fluidic multiplexors and/or other microfluidic structures for interfacing to a microchamber as described.

Readily available computational hardware resources using standard operating systems can be employed and modified according to the teachings provided herein, e.g., a PC (Intel x86 or Pentium chip-compatible DOS,™ OS2,™ WINDOWS,™ WINDOWS NT,™ WINDOWS95,™ WINDOWS98,™ LINUX, or even Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the data and/or statistical analysis can be constructed by one of skill using a standard programming language such as Visual Basic, Fortran, Basic, Java, or the like. Such software can also be constructed utilizing a variety of statistical programming languages, toolkits, or libraries.

Figure 21:
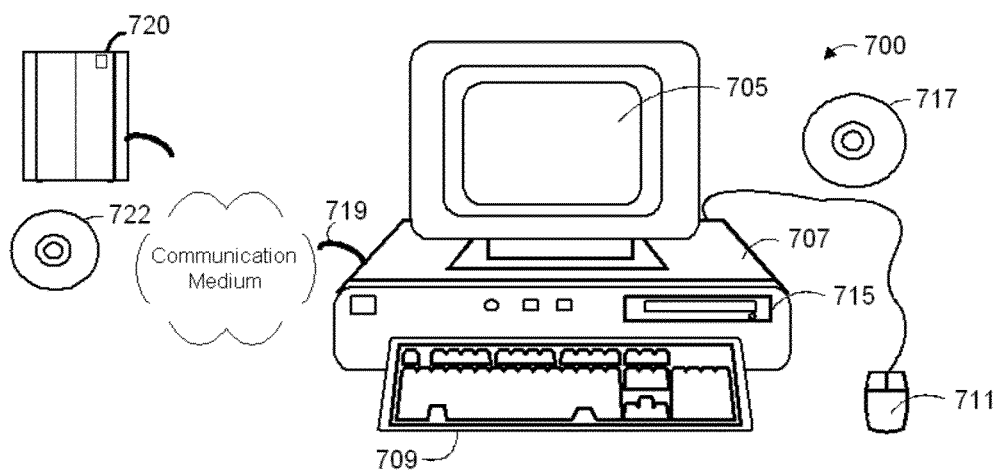
FIG. 21 is a block diagram showing a representative example logic device in which various aspects of the present invention may be embodied.

FIG. 21 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention are also included in the computer systems of the invention.

OTHER EMBODIMENTS

Although the present invention has been described in terms of various specific embodiments, it is not intended that the invention be limited to these embodiments. Modification within the spirit of the invention will be apparent to those skilled in the art.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed is:

1. A method for culturing and monitoring cells using a microfluidic cell culture system, wherein the microfluidic cell culture system comprises a cell chamber, separated from a first microfluidic flow channel by a perfusion barrier and from a second microfluidic flow channel by a second perfusion barrier on an opposite side of the cell chamber, a gravity flow inlet well, and an outlet well, the method comprising:
    introducing one or more groups of cells into the cell chamber of the microfluidic cell culture system;
    culturing the one or more groups of cells in the cell chamber;
    continuously perfusing the cultured one or more groups of cells by supplying a media solution to the gravity flow inlet well, wherein a medium level difference between the gravity flow inlet well and outlet well creates a perfusion flow rate;
    creating and controlling a first gradient in the cell chamber by supplying a first substance to the first microfluidic flow channel and a second substance to the second microfluidic flow channel, the first gradient forming within the cell chamber perpendicular to the first perfusion barrier and the second perfusion barrier;
    creating and controlling a second gradient in the cell chamber, after a selected period of time, by supplying a third substance to the first microfluidic flow channel and a fourth substance to the second microfluidic flow channel, the second gradient forming within the cell chamber perpendicular to the first perfusion barrier and the second perfusion barrier;
    wherein the cell chamber provides an uninterrupted optical path to the cultured one or more cells during culturing and creation and control of the gradients;
    capturing a plurality of images of the cultured one or more cells in the microfluidic culture system during culturing and during control of the gradients;
    using an information system to analyze the cultured one or more cells in a sequence of the plurality of images to determine migration properties of the cultured one or more cells in response to the first and second gradients.

2. The method of claim 1, wherein one or more of the microfluidic flow channels is associated with one or more barriers that restrict cell movement while introducing substances into the cell chamber.

3. The method of claim 1 further comprising:
    controlling gradient parameters to provide a steady state or varying gradient or both at different time periods.

4. The method of claim 1 further comprising:
    using microfluidic control of cell culture conditions and chemoattractant gradient formation during image capture to determine precise, dynamic quantitation of cell migration in response to stimuli.

5. The method of claim 1 further comprising:
    distinguishing chemotaxis towards a substance from non-directional migration by analyzing movements in a direction perpendicular to a gradient separately from movements in a direction parallel to the gradient.

6. The method of claim 1 further comprising:
    determining total migration distance and Euclidean distance with respect to gradient conditions.

7. The method of claim 1 further comprising:
    determining the effects of signaling molecules, growth factors, or other substances, on migration propensities of cells in one or more of tumors, wounds, developing tissues, immune responses, and other biological systems that can be characterized with respect to active cell migration.

8. The method of claim 1 further comprising:
    culturing cells in three distinct phases:
        complete substance feeding;
        serum starvation; and
        exposure to a chemoattractant.

9. The method of claim 1 wherein
    the first microfluidic channel is in communication with a first and second solution inlet well;
    the second microfluidic channel is in communication with a third and fourth solution inlet well; and
    the first gradient is created by supplying solutions from the first and third solution inlet wells and
    the second gradient is created by supplying solutions from the second and fourth solution inlet wells.

10. The method of claim 9, wherein complete medium is provided in the first and fourth solution inlet wells, and complete medium without chemoattractant is provided in the second and third solution inlet wells.

11. The method of claim 1 wherein the selected period of time is a sufficient time to determine cell migration or other properties in one direction of a gradient.

12. The method of claim 1 further comprising:
    capturing time-lapse images during a gradient portion or culture portion and storing digital representations of the images for analysis;

wherein images are captured at desired intervals during a gradient exposure time or a culture time or both;
analyzing the images using an information system;
wherein one or more individual cells are tracked for migratory properties across a sequential series or other series of images.

13. The method of claim 12, further comprising:
wherein desired intervals are any number between 1 minute and 48 hour intervals;
wherein individual cells comprise one or more of about 10, about 20, about 30, about 40, about 50, about 60-100, or about 100-5,000 representative cells;
wherein the series of images are any desired regular or irregular capture of images during any desired culture period.

14. The method of claim 1 further wherein one or more individual cells are monitored in response to gradients over the course of a period of between about 6 hours to about 6 days.

15. The method of claim 1 further comprising:
analyzing cell migration properties by comparing cells in stable medium to equivalent cells exposed to a nutrient or other gradient.

16. The method of claim 1 further comprising:
analyzing cell migration properties to determine when cell migration is significantly more directed, thereby indicating a response to a gradient in the culture chamber.

17. The method of claim 1 further comprising:
determining cell migration in response to a gradient by comparing cells in a constant substance and determining whether cells in the gradient are moving substantially farther away from their site of origin than cells in a constant substance state.

18. The method of claim 1 further comprising:
determining cell migration in response to a gradient by comparing a velocity of cells in a constant substance and a velocity of cells in the gradient.

19. The method of claim 1 further comprising culturing cells for a period of between 4 hours and 6 days that allows for both cell expansion and movement with images taken some period after gradient induction.

20. A method for culturing and monitoring cells using microfluidic cell culture systems comprising:
culturing cells within a cell chamber of a microfluidic cell culture system, the cell chamber comprising a first perfusion barrier in communication with a first microfluidic flow channel and a second perfusion barrier positioned opposite from the first perfusion barrier and in communication with a second microfluidic flow channel;
continuously perfusing cells with media using gravity-driven perfusion;
creating and controlling a gradient in the cell chamber by supplying a first substance to the first microfluidic flow channel and a second substance to the second microfluidic flow channel, the gradient forming within the cell chamber along a Y-axis towards the first perfusion barrier;
monitoring cells to determine their movement in response to the gradient;
detecting, for cells exposed to the gradient, movement of cells along the Y-axis toward the first barrier of the cell chamber in the positive direction of the gradient;
monitoring one or more control cells cultured in the absence of the gradient to detect less movement with far more random directional properties;
wherein cells exposed to the gradient are determined to move preferentially toward the source of higher gradient concentration; and
wherein both cell expansion and movement occurred during the 4 hour to 6 day intervals, with images taken some period after gradient creation.

21. The method of claim 10, where the chemoattractant is fetal bovine serum (FBS).

22. A method of analyzing cells exposed to a gradient in a microfluidic device, comprising:
culturing cells within a cell chamber of a microfluidic device;
supplying a first substance to a first microfluidic flow channel in communication with a first perfusion barrier, the first perfusion barrier separating the first microfluidic flow channel from a cell chamber;
supplying a second substance to a second microfluidic flow channel in communication with a second perfusion barrier, the second perfusion barrier spaced opposite from the first perfusion barrier and separating the second microfluidic flow channel from the cell chamber;
wherein the first substance passes at least in part through the first perfusion barrier into the cell chamber, and the second substance passes at least in part through the second perfusion barrier into the cell chamber, the first and second substances forming a first gradient within the cell chamber, the first gradient established perpendicular to the first perfusion barrier and second perfusion barrier; and
analyzing a response of the cultured cells within the cell chamber in response to the first gradient.

23. The method of claim 22, wherein the response of the cultured cells is at least one of cell movement and cell expansion.

24. The method of claim 22, further comprising:
supplying a third substance to the first microfluidic flow channel;
supplying a fourth substance to the second microfluidic channel;
such that the third substance passes at least in part through the first perfusion barrier into the cell chamber, and the fourth substance passes at least in part through the second perfusion barrier into the cell chamber, the third and fourth substances forming a second gradient within the cell chamber; and
analyzing a response of the cultured cells within the cell chamber in response to the second gradient.

25. The method of claim 24, wherein the second gradient is created concurrently with the first gradient.

26. The method of claim 22, wherein the cultured cells migrate in a profile that is substantially linear in an axis perpendicular to the first perfusion barrier and second perfusion barrier.

* * * * *